US011401316B2

(12) United States Patent
Blankenstein et al.

(10) Patent No.: US 11,401,316 B2
(45) Date of Patent: Aug. 2, 2022

(54) HIGH AVIDITY HPV T-CELL RECEPTORS

(71) Applicant: MAX-DELBRUECK-CENTRUM FUER MOLEKULARE MEDIZIN IN DER HELMHOLTZ-GEMEINSCHAFT, Berlin (DE)

(72) Inventors: Thomas Blankenstein, Berlin (DE); Gerald Willimsky, Berlin (DE)

(73) Assignee: MAX-DELBRUECK-CENTRUM FUER MOLEKULARE MEDIZIN IN DER HELMHOLTZ-GEMEINSCHAFT, Berlin (DE)

( * ) Notice: Subject to any disclaimer, the term of this patent is extended or adjusted under 35 U.S.C. 154(b) by 57 days.

(21) Appl. No.: 15/768,740

(22) PCT Filed: Oct. 13, 2016

(86) PCT No.: PCT/EP2016/074612
§ 371 (c)(1),
(2) Date: Apr. 16, 2018

(87) PCT Pub. No.: WO2017/064198
PCT Pub. Date: Apr. 20, 2017

(65) Prior Publication Data
US 2019/0062398 A1     Feb. 28, 2019

(30) Foreign Application Priority Data
Oct. 16, 2015  (EP) ..................... 15190230

(51) Int. Cl.
*A61P 31/20* (2006.01)
*C07K 14/005* (2006.01)
*C07K 14/725* (2006.01)
*C12N 5/0783* (2010.01)
*C07K 16/08* (2006.01)
*A61K 39/12* (2006.01)
*A61K 39/00* (2006.01)
*A61K 48/00* (2006.01)

(52) U.S. Cl.
CPC .......... *C07K 14/7051* (2013.01); *A61K 39/12* (2013.01); *A61P 31/20* (2018.01); *C07K 14/005* (2013.01); *C07K 16/08* (2013.01); *C07K 16/084* (2013.01); *C12N 5/0636* (2013.01); *A61K 48/00* (2013.01); *A61K 2039/5156* (2013.01); *A61K 2039/5158* (2013.01); *A61K 2039/585* (2013.01); *C07K 2317/565* (2013.01); *C07K 2318/00* (2013.01); *C12N 2510/00* (2013.01); *C12N 2710/20034* (2013.01)

(58) Field of Classification Search
None
See application file for complete search history.

(56) References Cited

U.S. PATENT DOCUMENTS

2015/0337369 A1*  11/2015  Davis ................. C12Q 1/686
                                                              506/2

FOREIGN PATENT DOCUMENTS

| WO | WO-2009042570 A2 * | 4/2009 | ........... C07K 14/705 |
|----|---------------------|--------|-------------------------|
| WO | 2012/038055 A1      | 3/2012 | |
| WO | 2015/009606         | 1/2015 | |
| WO | 2015/092362 A1      | 6/2015 | |

OTHER PUBLICATIONS

Woodsworth (Genome Medicine, 5(98): 2013) (Year: 2013).*
Bolotin (Eur J Immunol, 42: 3073-3083, 2012) (Year: 2012).*
Ritmahan (Immunogenetics (2020) 72:109-118) (Year: 2020).*
Padlan (Advances in Biochemstry, 49: 57-133, 1996) (Year: 1996).*
MacCallum et al. (J. Mol. Biol. (1996) 262:732-745), (Year: 1996).*
Dendrou (Nature Reviews, Immunology, 18: 325-330, 2018) (Year: 2018).*
Gras (J. Exp. Med. 207(7): 1555-1567, 2010 (Year: 2010).*
Schmitt (Clin Cancer Res; 21(23); 5191-7, AACR, 2015) (Year: 2015).*
International Search Report and Written Opinion; International Patent Application No. PCT/EP2016/074612, dated Dec. 13, 2016 (13 pages).
Extended European Search Report; European Patent Application No. 16781446.6; dated May 24, 2019 (7 pages).

* cited by examiner

*Primary Examiner* — Anoop K Singh
*Assistant Examiner* — Magdalene K Sgagias
(74) *Attorney, Agent, or Firm* — Hamre, Schumann, Mueller & Larson, P.C.

(57) ABSTRACT

The present invention pertains to novel high avidity antigen recognizing constructs against Human Papilloma Virus antigens. The invention provides novel T cell receptor (TCR) based molecules which are selective and specific for HPV 16/18 proteins E5, E6 and E7. The TCR of the invention, and HPV antigen-binding fragments derived therefrom, are of use for the diagnosis, treatment and prevention of HPV infection, as well as for the diagnosis, treatment and prevention of HPV infection mediated secondary diseases as HPV infection caused cancers, such as cervical, nasopharyngeal or head and neck cancer. Further provided are nucleic acids encoding the proteins of the invention, and recombinant cells expressing the same.

Figure 1:
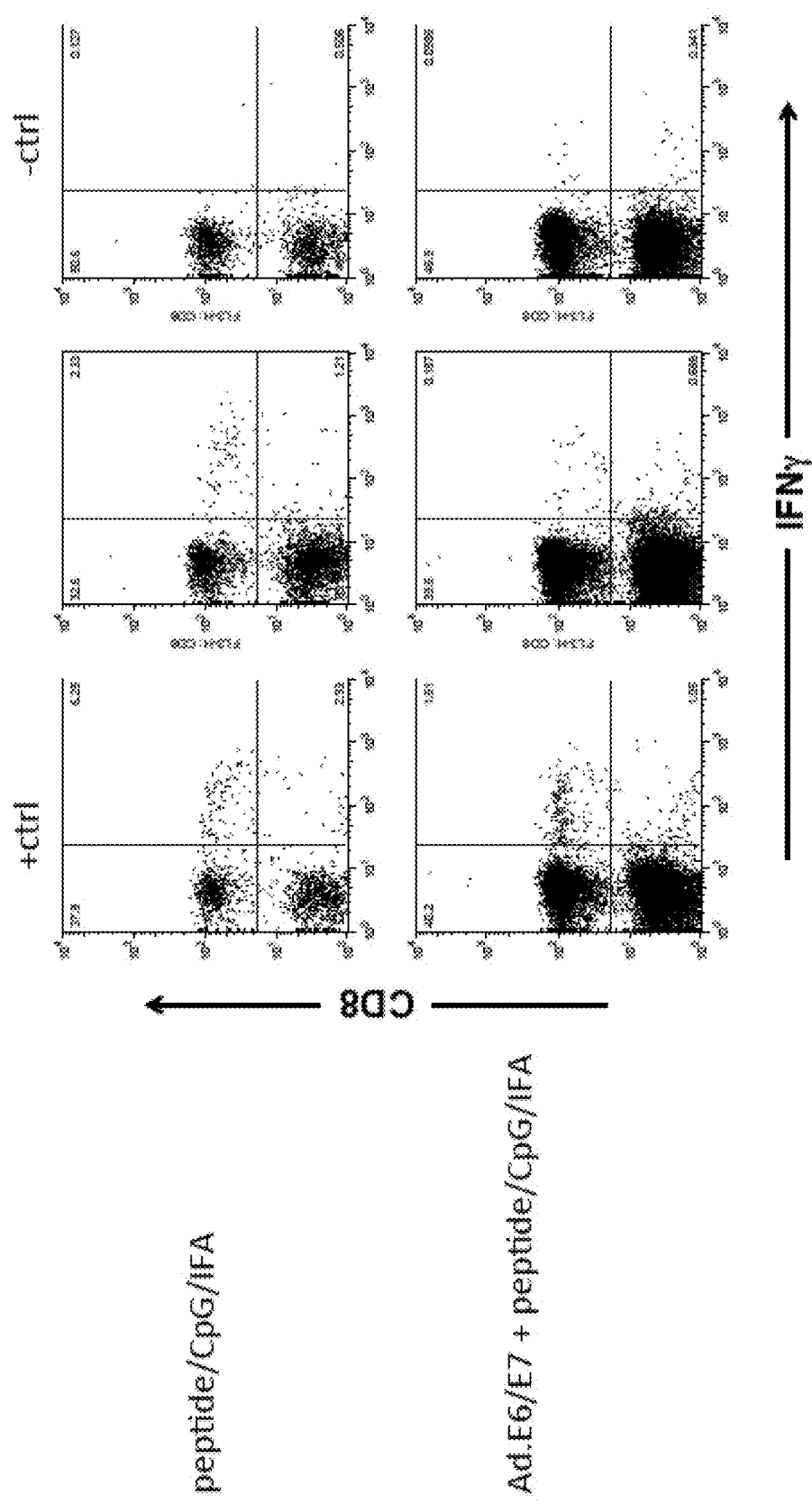

19 Claims, 7 Drawing Sheets
Specification includes a Sequence Listing.

HIGH AVIDITY HPV T-CELL RECEPTORS

FIELD OF THE INVENTION

The present invention pertains to novel high avidity antigen recognizing constructs against Human Papilloma Virus antigens. The invention provides novel T cell receptor (TCR) based molecules which are selective and specific for HPV 16/18 proteins E5, E6 and E7. The TCR of the invention, and HPV antigen-binding fragments derived therefrom, are of use for the diagnosis, treatment and prevention of HPV infection, as well as for the diagnosis, treatment and prevention of HPV infection mediated secondary diseases as HPV infection caused cancers, such as cervical, nasopharyngeal or head and neck cancer. Further provided are nucleic acids encoding the proteins of the invention, and recombinant cells expressing the same.

DESCRIPTION

A TCR is a heterodimeric cell surface protein of the immunoglobulin super-family which is associated with invariant proteins of the CD3 complex involved in mediating signal transduction. TCRs exist in αβ and γδ forms, which are structurally similar but have quite distinct anatomical locations and probably functions. The extracellular portion of native heterodimeric αβTCR consists of two polypeptides, each of which has a membrane-proximal constant domain, and a membrane-distal variable domain. Each of the constant and variable domains includes an intra-chain disulfide bond. The variable domains contain the highly polymorphic loops analogous to the complementarity determining regions (CDRs) of antibodies. The use of TCR gene therapy overcomes a number of current hurdles. It allows equipping patients' own T cells with desired specificities and generation of sufficient numbers of T cells in a short period of time, avoiding their exhaustion. The TCR will be transduced into central memory T cells or T cells with stem cell characteristics, which may ensure better persistence and function upon transfer. TCR-engineered T cells will be infused into cancer patients rendered lymphopenic by chemotherapy or irradiation, allowing efficient engraftment but inhibiting immune suppression.

Human papillomaviruses (HPV) are small, non-enveloped, double-stranded DNA viruses that infect the cutaneous and/or mucosal epithelium. Over 100 HPV genotypes are known to exist. A subset of HPVs that are mucosotropic, infecting the anogenital tract of men and women, are the most common sexually transmitted human pathogens. These sexually transmitted, mucosotropic HPVs are further sub-categorized as high risk (e.g. HPV16 and HPV18) or low risk (HPV6 and HPV11) depending on their oncogenicity. High risk genotypes are causally associated with anogenital cancers including nearly 100% of cervical carcinomas, the second leading cause of death from cancer in women worldwide.

The persistence of oncogenic HPV is necessary for the development of cervical precancer and cancer. However, the factors that determine viral persistence and tumorigenic progression are not fully understood. The initial events of cervical carcinogenesis after viral infection depend on the fact that high-risk HPV types undergo specific changes that abrogate the transcriptional control of viral gene expression in the infected keratinocytes. Inactivation of these cellular control functions permits deregulated transcription of the early viral genes E6 and E7, thereby triggering cell proliferation, inhibition of apoptosis, reprogramming of differentiation and chromosomal instability. These changes can support the integration of episomal HPV genomes into chromosomes of the host cell, and contribute to further overexpression of the viral genes E6 and E7, resulting in an increase of the E7 oncoprotein levels during early steps of cervical carcinogenesis.

That the viral oncoproteins E6 and E7 are crucial during carcinogenesis was further proven by the fact that high-risk E7 protein, in cooperation with high-risk E6, can efficiently immortalize human primary keratinocytes in vitro. Moreover, the consistent overexpression of the E6 and E7 oncogenes is required to induce and to maintain the transformed phenotype of cervical cancer cells.

Therefore, the detection of E6 and E7 protein seems to be the superior diagnostic tool. Various antibodies are already known in the art, but they either display low sensitivity or specificity or are described to cross-react with the E7 proteins of various HPV types. Also, as polyclonal antibodies can only be produced in a limited quantity by one animal, there are batch-to-batch differences. The difficulty to produce highly specific and sensitive monoclonal antibodies against E7 proteins is mainly due to the low immunogenicity of E7 proteins.

One object of the present invention is therefore to overcome the aforementioned difficulties and to provide highly specific and more sensitive means for a cost-efficient, rapid and reliable diagnosis of HPV infections, for example via detection of the presence or absence of an early HPV protein such as E5, E6 or E7.

While an effective prophylactic vaccine against two of the most common high risk HPVs is now available, the high cost, issues with social acceptance, and limitations in health care systems through which the vaccine can be provided will likely limit the availability of this vaccine to women particularly in developing countries where HPV-associated anogenital cancers are most commonly found. Consequently there remains a need to identify direct treatments to target HPV infection and cancers that stem from HPV infections such as cervical cancer. Hence, another technical problem the present invention seeks to solve is to provide effective and high avidity T cell receptor based molecules that are of use for therapeutic approaches in the treatment and prevention of HPV mediated diseases.

The above problems are solved in a first aspect by an antigen recognizing construct comprising an amino acid sequence having at least 50%, 60%, 70%, 80%, 90%, 95%, 98%, 99% or 100% sequence identity to an amino acid sequence selected from SEQ ID Nos. 9 to 28.

SEQ ID Nos 9 to 28 correspond to TCR T1 to T9 CDR3 regions as shown in the tables of the example section of this application (examples 1 to 9). It was surprisingly discovered that the HPV responsive TCRs of the invention are highly avid compared to state of the art TCRs directed at HPV antigens. In some instances the TCR of the invention are more specific, more sensitive, more selective and/or more avid compared to state of the art TCR. In one preferred embodiment of the present invention the antigen recognizing construct comprises a complementary determining region 3 (CDR3) having at least 50%, 60%, 70%, 80%, 90%, 95%, 98%, 99% or 100% sequence identity to an amino acid sequence selected from SEQ ID Nos. 9 to 28.

The CDR3 of the antigen recognizing construct of the invention may be mutated. Mutations of the CDR3 sequences of SEQ ID NOs: 9 to 28 preferably include a substitution, deletion, addition, or insertion of not more than three, preferably two, and most preferably not more than one amino acid residue.

In another additional or alternative embodiment, the antigen recognizing construct is an HPV antigen recognizing construct.

In another additional or alternative embodiment, the antigen recognizing construct may further comprise a CDR1 and a CDR2 domain sequence. Within the variable domain, CDR1 and CDR2 are found in the variable (V) region of a polypeptide chain, and CDR3 includes some of V, all of diversity (D) and joining (J) regions. CDR3 is the most variable and is the main CDR responsible for recognizing the antigen. CDR1 and CDR2 sequences may be selected from a CDR sequence of a human variable chain allele.

Native alpha-beta heterodimeric TCRs have an alpha chain and a beta chain. Each chain comprises variable, joining and constant regions, and the beta chain also usually contains a short diversity region between the variable and joining regions, but this diversity region is often considered as part of the joining region. Each variable region comprises three CDRs (Complementarity Determining Regions) embedded in a framework sequence, one being the hypervariable region named CDR3. There are several types of alpha chain variable (Vα) regions and several types of beta chain variable (Vβ) regions distinguished by their framework, CDR1 and CDR2 sequences, and by a partly defined CDR3 sequence. The Vα types are referred to in IMGT nomenclature by a unique TRAV number, VP types are referred to by a unique TRBV number.

Therefore, in one additional or alternative embodiment the antigen recognizing construct of the invention comprises CDR1, CDR2 and CDR3 sequences in a combination as provided by the tables of the example section which display the respective variable chain allele together with the CDR3 sequence. Therefore, preferred are antigen recognizing constructs of the invention that comprise at least one, preferably all three CDR sequences CDR1, CDR2 and CDR3.

In one embodiment of the invention the antigen recognizing construct specifically binds to a human papillomavirus (HPV) antigen; preferably wherein the HPV antigen is a protein selected from HPV 16 E5, HPV 16 E6, HPV 16 E7, HPV 18 E6 and HPV 18 E7.

The term "specificity" or "antigen specificity" or "specific for" a given antigen, as used herein means that the antigen recognizing construct can specifically bind to said antigen, preferably a HPV antigen, more preferably with high avidity. For example, a TCR may be considered to have "antigenic specificity" for HPV antigens if T cells expressing the TCR secrete at least about 200 pg/ml or more (e.g., 250 pg/ml or more, 300 pg/ml or more, 400 pg/ml or more, 500 pg/ml or more, 600 pg/ml or more, 700 pg/ml or more, 1000 pg ml or more, 2,000 pg/ml or more, 2,500 pg/ml or more, 5,000 pg/ml or more) of interferon γ (IFN-γ) upon co-culture with target cells pulsed with a low concentration of a HPV antigen, such as the HPV 16 E5, E6 and E7 antigens provided herein below (e.g., about 10-11 mol/l, 10-10 mol/l, 10-9 mol/l, 10-8 mol/l, 10-7 mol/l, 10-6 mol/l, 10-5 mol/l). Alternatively or additionally, a TCR may be considered to have "antigenic specificity" for HPV if T cells expressing the TCR secrete at least twice as much IFN-γ as the untransduced background level of IFN-γ upon co-culture with target cells pulsed with a low concentration of HPV antigens. Such a "specificity" as described above can—for example—be analyzed with an ELISA.

In one alternative or additional embodiment of the invention the antigen recognizing construct selectively binds to a human papillomavirus (HPV) antigen; preferably wherein the HPV antigen is a protein selected from HPV 16 E5, HPV 16 E6, HPV 16 E7, HPV 18 E6 and HPV 18 E7.

The term "selectivity" or "selective recognising/binding" is understood to refer to the property of an antibody or T-cell receptor to selectively recognise or bind to preferably only one specific epitope and preferably shows no or substantially no cross-reactivity to another epitope. Preferably "selectivity" or "selective recognising/binding" means that the antigen recognizing construct (e.g. a TCR) selectively recognises or binds to preferably only one specific epitope and preferably shows no or substantially no cross-reactivity to another epitope, wherein said epitope is unique for one protein, such that the antigen recognizing construct shows no or substantially no cross-reactivity to another epitope and another protein.

The antigen recognizing construct according to the invention is preferably selected from an antibody, or derivative or fragment thereof, or a T cell receptor (TCR), or derivative or fragment thereof. A derivative or fragment of an antibody or TCR of the invention shall preferably retain the antigen binding/recognizing ability of the parent molecule, in particular its specificity and/or selectivity as explained above.

In an embodiment of the invention, the inventive TCRs are able to recognize HPV antigens in a major histocompatibility complex (MHC) class I-dependent manner. "MHC class I-dependent manner," as used herein, means that the TCR elicits an immune response upon binding to HPV antigens within the context of an MHC class I molecule. The MHC class I molecule can be any MHC class I molecule known in the art, e.g., HLA-A molecules. In a preferred embodiment of the invention, the MHC class I molecule is an HLA-A2 molecule, preferably HLA type A2.01.

The following epitopes (SEQ ID NO: 1 to 9) were used to generate the TCR of the examples: YIIFVYIPL (HPV 16 $E5_{63-71}$), KLPQLCTEL (HPV 16 $E6_{11-19}$), TIHDIILECV (HPV 16 $E6_{29-30}$), YMLDLQPET (HPV 16 $E7_{11-19}$), YMLDLQPETT (HPV 16 $E7_{11-20}$), TLGIVCPI (HPV 16 $E7_{86-93}$), KCIDFYSRI (HPV 18 $E6_{67-75}$), FQQLFLNTL (HPV 18 $E7_{86-94}$). Thus, one embodiment of the invention described antigen recognizing constructs, which are specific and/or selective for one of the above HPV epitopes. The person of skill knows that depending on which CDR3 is present, the antigen recognizing construct of the invention binds specifically and/or selectively to its respective epitope as disclosed in the example section.

The invention provides both single chain antigen recognizing construct and double chain recognizing constructs.

The invention in particular provides a TCR as antigen recognizing construct, or fragment or derivative thereof. The TCR preferably is human, which is understood as being generated from a human TCR locus and therefore comprising human TCR sequences. Furthermore, the TCR of the invention may be characterized in that it is of human origin and specifically recognizes an HPV antigen. The term "origin" in this respect refers to a mutated sequence which is derived from the respective "original" sequence but contains amino acid alterations. For example, a TCR of human origin may comprise TCR sequences of a non-human species and that were artificially introduced into the human TCR sequence.

Another embodiment of the invention additionally or alternatively provides the antigen recognizing construct described above which induces an immune response, preferably wherein the immune response is characterized by an increase in interferon (IFN) γ levels.

TCRs of the invention may be provided as single chain α or β molecules, or alternatively as double chain constructs composed of both the α and β chain, or γ and δ chain. Hence, the TCR of the invention preferably comprises in its alpha chain a CDR3 having at least 50%, 60%, 70%, 80%, 90%, 95%, 98%, 99%, or 100% sequence identity to an amino acid sequence selected from SEQ ID Nos. 9, 10, 12, 14, 16, 18, 21, 23, 25, 27, and/or comprises in its beta chain an CDR3 having at least 50%, 60%, 70%, 80%, 90%, 95%, 98%, 99%, or 100% sequence identity to an amino acid sequence selected from SEQ ID Nos.11, 13, 15, 17, 19, 20, 22, 24, 26, 28.

Preferably the double chain TCR, or antigen binding fragment thereof, comprises in a first polypeptide chain the amino acid sequence according to SEQ ID NO: 9, and in a second polypeptide chain the amino acid sequence according to SEQ ID NO: 11; or in a first polypeptide chain the amino acid sequence according to SEQ ID NO: 10, and in a second polypeptide chain the amino acid sequence according to SEQ ID NO: 11; or in a first polypeptide chain the amino acid sequence according to SEQ ID NO: 12, and in a second polypeptide chain the amino acid sequence according to SEQ ID NO: 13; or in a first polypeptide chain the amino acid sequence according to SEQ ID NO: 14, and in a second polypeptide chain the amino acid sequence according to SEQ ID NO: 15; or in a first polypeptide chain the amino acid sequence according to SEQ ID NO: 16, and in a second polypeptide chain the amino acid sequence according to SEQ ID NO: 17; or in a first polypeptide chain the amino acid sequence according to SEQ ID NO: 18, and in a second polypeptide chain the amino acid sequence according to SEQ ID NO: 19; or in a first polypeptide chain the amino acid sequence according to SEQ ID NO: 18, and in a second polypeptide chain the amino acid sequence according to SEQ ID NO: 20; or in a first polypeptide chain the amino acid sequence according to SEQ ID NO: 21, and in a second polypeptide chain the amino acid sequence according to SEQ ID NO: 22; or in a first polypeptide chain the amino acid sequence according to SEQ ID NO: 23, and in a second polypeptide chain the amino acid sequence according to SEQ ID NO: 24; or in a first polypeptide chain the amino acid sequence according to SEQ ID NO: 25, and in a second polypeptide chain the amino acid sequence according to SEQ ID NO: 26; or in a first polypeptide chain the amino acid sequence according to SEQ ID NO: 27, and in a second polypeptide chain the amino acid sequence according to SEQ ID NO: 28. Any one of the aforementioned double chain TCR, or antigen binding fragments thereof, are preferred TCR of the present invention. In some embodiments the CDR3 of the double chain TCR of the invention may be mutated. Mutations of the CDR3 sequences of SEQ ID NOs: 9 to 28 as provided above preferably include a substitution, deletion, addition, or insertion of not more than three, preferably two, and most preferably not more than one amino acid residue. In some embodiments the first polypeptide chain may be a TCR α or γ chain, and the second polypeptide chain may be a TCR β or δ chain. Preferred is the combination of an αβ or γδ TCR.

The TCR, or the antigen binding fragment thereof, is composed of a TCR α and a TCR β chain, or γ and δ chain. Such a double chain TCR comprises within each chain variable regions comprising CDR1, CDR2 and CDR3 sequences. The TCRs comprises the CDR1 to 3 sequences as comprised in the variable chain amino acid sequence shown in SEQ ID NO: 29 and SEQ ID NO: 31 (T1a), or SEQ ID NO: 30 and SEQ ID NO: 31 (T1b); or SEQ ID NO: 32 and SEQ ID NO: 33 (T2); or SEQ ID NO: 34 and SEQ ID NO: 35 (T3); or SEQ ID NO: 36 and SEQ ID NO: 37 (T4); or SEQ ID NO: 38 and SEQ ID NO: 39 (T5a); or SEQ ID NO: 38 and SEQ ID NO: 40 (T5b); or SEQ ID NO: 41 and SEQ ID NO: 42 (T6); or SEQ ID NO: 43 and SEQ ID NO: 44 (T7); or SEQ ID NO: 45 and SEQ ID NO: 46 (T8); or SEQ ID NO: 47 and SEQ ID NO: 48 (T9).

Some embodiments of the invention pertain to a TCR, or a fragment thereof, composed of a TCR α and a TCR β chain, wherein said TCR comprises the variable region sequences of the α and β chain according to SEQ ID NO: 29 and 31 respectively (T1a), or 30 and 31 (T1b); or 32 and 33 (T2); or 34 and 35 (T3); or 36 and 37 (T4); or 38 and 39 (T5a); or 38 and 40 (T5b); or 41 and 42 (T6); or 43 and 44 (T7); or 45 and 46 (T8); or 47 and 48 respectively (T9).

The inventive TCRs may further comprise a constant region derived from any suitable species such as, e.g., human or mouse. In an embodiment of the invention, the inventive TCRs further comprise a human constant region. In some preferred embodiments the constant region of the TCR of the invention may be slightly modified, for example by the introduction of murine sequences which may increase TCR stability.

As used herein, the term "murine" or "human," when referring to an antigen recognizing construct, or a TCR, or any component of a TCR described herein (e.g., complementarity determining region (CDR), variable region, constant region, α chain, and/or β chain), means a TCR (or component thereof) which is derived from a mouse or a human unrearranged TCR locus, respectively.

In an embodiment of the invention, the chimeric TCR can comprise an α chain of a TCR and a β chain of a TCR. Each of the α chain and β chain of the inventive chimeric TCR can independently comprise any amino acid sequence. Preferably, the α chain comprises the human variable region of an α chain and the murine constant region of an α chain as set forth above.

In one embodiment the TCR of the invention is a human TCR comprising human variable regions according to the above embodiments and human constant regions.

The TCR of the invention may be provided as a single chain TCR (scTCR). A scTCR can comprise a polypeptide of a variable region of a first TCR chain (e.g., an alpha chain) and a polypeptide of an entire (full-length) second TCR chain (e.g., a beta chain), or vice versa. Furthermore, the scTCR can optionally comprise one or more linkers which join the two or more polypeptides together. The linker can be, for instance, a peptide which joins together two single chains, as described herein. Also provided is such a scTCR of the invention, which is fused to a human cytokine, such as IL-2, IL-7 or IL-15.

The antigen recognizing construct according to the invention can also be provided in the form of a multimeric complex, comprising at least two scTCR molecules, wherein said scTCR molecules are each fused to at least one biotin moiety, and wherein said scTCRs are interconnected by biotin-strepavidin interaction to allow the formation of said multimeric complex. Similar approaches for the generation of multimeric TCR are also possible and included by the disclosure. Also provided are multimeric complexes of a higher order, comprising more than two scTCR of the invention.

For the purposes of the present invention, a TCR is a moiety having at least one TCR alpha and/or TCR beta variable domain. Generally they comprise both a TCR alpha variable domain and a TCR beta variable domain. They may be αβ heterodimers or may be single chain format. For use in adoptive therapy, an αβ heterodimeric TCR may, for example, be transfected as full length chains having both cytoplasmic and transmembrane domains. If desired, an introduced disulfide bond between residues of the respective constant domains may be present.

In one additional preferred embodiment of the first aspect of the invention, the antigen recognizing construct is as described above a TCR. The TCR preferably comprises at least one alpha and/or beta TCR chain, wherein said TCR chain comprises an amino acid sequence according to any one of the TCR chains shown in SEQ ID Nos. 22-39, or an amino acid sequence having at least 50%, 60%, 70%, 80%, 90%, 95%, 98%, 99% or 100% identity to an amino acid sequence shown in SEQ ID No. 22 to 39.

In a preferred embodiment the antigen recognizing construct is a human TCR, or fragment or derivative thereof. A human TCR or fragment or derivative thereof is a TCR which comprises over 50% of the corresponding human TCR sequence. Preferably only a small part of the TCR sequence is of artificial origin or derived from other species. It is known however, that chimeric TCRs e.g. from human origin with murine sequences in the constant domains, are advantageous. Particularly preferred are therefore TCRs in accordance with the present invention, which contain murine sequences in the extracellular part of their constant domains.

Thus, it is also preferred that the inventive antigen recognizing construct is able to recognize its antigen in a human leucocyte antigen (HLA) dependent manner, preferably in a HLA-A02 dependent manner. The term "HLA dependent manner" in the context of the present invention means that the antigen recognizing construct binds to the antigen only in the event that the antigenic peptide is presented by HLA.

The antigen recognizing construct in accordance with the invention in one embodiment preferably induces an immune response, preferably wherein the immune response is characterized by the increase in interferon (IFN) γ levels.

Also provided by the invention is a polypeptide comprising a functional portion of any of the TCRs (or functional variants thereof) described herein, for examples of any one of the TCRs T1 to T9 as provided in the example section. The term "polypeptide" as used herein includes oligopeptides and refers to a single chain of amino acids connected by one or more peptide bonds. With respect to the inventive polypeptides, the functional portion can be any portion comprising contiguous amino acids of the TCR (or functional variant thereof) of which it is a part, provided that the functional portion specifically binds to a HPV antigen as disclosed in SEQ ID NO 1 to 8. The term "functional portion" when used in reference to a TCR (or functional variant thereof) refers to any part or fragment of the TCR (or functional variant thereof) of the invention, which part or fragment retains the biological activity of the TCR (or functional variant thereof) of which it is a part (the parent TCR or parent functional variant thereof). Functional portions encompass, for example, those parts of a TCR (or functional variant thereof) that retain the ability to specifically bind to a HPV antigen (e.g., SEQ ID NO 1 to 8, in an HLA-A2-dependent manner), or detect, treat, or prevent cancer, to a similar extent, the same extent, or to a higher extent, as the parent TCR (or functional variant thereof). In reference to the parent TCR (or functional variant thereof), the functional portion can comprise, for instance, about 10%, 25%, 30%, 50%, 68%, 80%, 90%, 95%, or more, of the parent TCR variable sequences (or functional variant thereof).

The functional portion can comprise additional amino acids at the amino or carboxy terminus of the portion, or at both termini, which additional amino acids are not found in the amino acid sequence of the parent TCR or functional variant thereof. Desirably, the additional amino acids do not interfere with the biological function of the functional portion, e.g., specifically binding to HPV antigens; and/or having the ability to detect cancer, treat or prevent cancer, etc. More desirably, the additional amino acids enhance the biological activity, as compared to the biological activity of the parent TCR or functional variant thereof.

The polypeptide can comprise a functional portion of either or both of the α and β chains of the TCRs or functional variant thereof of the invention, such as a functional portion comprising one of more of CDR1, CDR2, and CDR3 of the variable region(s) of the α chain and/or β chain of a TCR or functional variant thereof of the invention. In an embodiment of the invention, the polypeptide can comprise a functional portion comprising the amino acid sequence of SEQ ID NO: 9 to 28 (CDR3 of the variable regions of the TCR of the invention), or a combination thereof. In an embodiment of the invention, the inventive polypeptide can comprise, for instance, the variable region of the inventive TCR or functional variant thereof comprising a combination of the CDR regions set forth above. In this regard, the polypeptide can comprise the amino acid sequence of any of SEQ ID NO: 29 to 48 (the variable regions of an α or β chain).

In some instances, the construct of the invention may comprise one or two polypeptide chains comprising a sequences according to any of the SEQ ID NO: 9 to 48 (CDR sequences or whole variable regions), or functional fragments thereof, and further comprise(s) other amino acid sequences, e.g., an amino acid sequence encoding an immunoglobulin or a portion thereof, then the inventive protein can be a fusion protein. In this regard, the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof, including, but not limited to an immunoglobulin, CD3, CD4, CD8, an MHC molecule, a CD1 molecule, e.g., CD 1a, CD 1b, CD1c, CD Id, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods. In some embodiments of the invention, the TCRs (and functional portions and functional variants thereof), polypeptides, and proteins of the invention may be expressed as a single protein comprising a linker peptide linking the α/γ chain and the β/δ chain. In this regard, the TCRs (and functional variants and functional portions thereof), polypeptides, and proteins of the invention comprising the amino acid sequences of the variable regions of the TCR of the invention (T1 to T9) and may further comprise a linker peptide. The linker peptide may advantageously facilitate the expression of a recombinant TCR (including functional portions and functional variants thereof), polypeptide, and/or protein in a host cell. The linker peptide may comprise any suitable amino acid sequence. Linker sequences for single chain TCR constructs are well known in the art. Such a single chain construct may further comprise one, or two, constant domain sequences. Upon expression of the construct including the linker peptide by a host cell, the linker peptide may also be cleaved, resulting in separated α and β chains.

As already mentioned above, the binding functionality of the TCR of the invention may be provided in the framework of an antibody. The term "antibody" in its various grammatical forms is used herein to refer to immunoglobulin molecules and immunologically active portions of immunoglobulin molecules, i.e., molecules that contain an antibody combining site or a paratope. Such molecules are also referred to as "antigen binding fragments" of immunoglobulin molecules. The invention further provides an antibody, or antigen binding portion thereof, which specifically binds to the antigens described herein. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form.

The invention also provides antigen binding portions of any of the antibodies described herein. The antigen binding portion can be any portion that has at least one antigen binding site, such as Fab, F(ab')2, dsFv, sFv, diabodies, and triabodies. A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques. Similarly, disulfide-stabilized variable region fragments (dsFv) can be prepared by recombinant DNA technology, antibody fragments of the invention, however, are not limited to these exemplary types of antibody fragments. Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles). In some instances the TCR CDR3 sequence might be slightly modified, but preferably by not more than 3 amino acid residues, preferably only two and most preferably only one amino acid position, compared to the CDR3 sequences provided in SEQ ID NO 9 to 28. Preferably the antibodies comprise the CDR3, preferably all of CDR1 to CDR3 regions in the combination as indicated for the TCR T1 to T9 in the example section of this disclosure.

Suitable methods of making antibodies are known in the art. For instance, standard hybridoma methods are described in, e.g., Kohler and Milstein, Eur. J. Immunol, 5, 511-519 (1976), Harlow and Lane (eds.), Antibodies: A Laboratory Manual, CSH Press (1988), and C. A. Janeway et al. (eds.), Immunobiology, 8 Ed., Garland Publishing, New York, N.Y. (2011)). Alternatively, other methods, such as EBV-hybridoma methods (Haskard and Archer, J. Immunol. Methods, 74(2), 361-67 (1984), and Roder et al, Methods Enzymol, 121, 140-67 (1986)), and bacteriophage vector expression systems (see, e.g., Huse et al., Science, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1.

Some embodiments of the invention also pertain to TCRs, or functional fragments and polypeptides thereof, which are soluble TCRs. As used herein, the term "soluble T-cell receptor" refers to heterodimeric truncated variants of native TCRs which comprise extracellular portions of the TCR α-chain and β-chain linked by a disulfide bond, but which lack the transmembrane and cytosolic domains of the native protein. The terms "soluble T-cell receptor α-chain sequence and soluble T-cell receptor β-chain sequence" refer to TCR α-chain and β-chain sequences that lack the transmembrane and cytosolic domains. The sequence (amino acid or nucleic) of the soluble TCR α-chain and β-chains may be identical to the corresponding sequences in a native TCR or may comprise variant soluble TCR α-chain and β-chain sequences as compared to the corresponding native TCR sequences. The term "soluble T-cell receptor" as used herein encompasses soluble TCRs with variant or non-variant soluble TCR α-chain and β-chain sequences. The variations may be in the variable or constant regions of the soluble TCR α-chain and β-chain sequences and can include, but are not limited to, amino acid deletion, insertion, substitution mutations as well as changes to the nucleic acid sequence which do not alter the amino acid sequence. Soluble TCR of the invention in any case retain the binding functionality of their parent molecules.

The above problem is further solved by a nucleic acid encoding for an antigen recognizing construct of the invention, or any of the aforementioned protein or polypeptide constructs. The nucleic acid preferably (a) has a strand encoding for an antigen recognizing construct according to the invention; (b) has a strand complementary to the strand in (a); or (c) has a strand that hybridizes under stringent conditions with a molecule as described in (a) or (b). Stringent conditions are known to the person of skill in the art, specifically from Sambrook et al, "Molecular Cloning". In addition to that, the nucleic acid optionally has further sequences which are necessary for expressing the nucleic acid sequence corresponding to the protein, specifically for expression in a mammalian/human cell. The nucleic acid used can be contained in a vector suitable for allowing expression of the nucleic acid sequence corresponding to the peptide in a cell. However, the nucleic acids can also be used to transform a presenting cell, which shall not be restricted to classical antigen-presenting cells such as dendritic cells, in such a way that they themselves produce the corresponding proteins on their cellular surface.

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication. The nucleic acid can comprise any nucleotide sequence which encodes any of the TCRs, polypeptides, or proteins, or functional portions or functional variants thereof described herein.

Furthermore, the invention provides a vector comprising a nucleic acid in accordance to the invention as described above. Desirably, the vector is an expression vector or a recombinant expression vector. The term "recombinant expression vector" refers in context of the present invention to a nucleic acid construct that allows for the expression of an mRNA, protein or polypeptide in a suitable host cell. The recombinant expression vector of the invention can be any suitable recombinant expression vector, and can be used to transform or transfect any suitable host. Suitable vectors include those designed for propagation and expansion or for expression or both, such as plasmids and viruses. Examples of animal expression vectors include pMP71, pEUK-Cl, pMAM, pMAMneo and pSB100Xo. Preferably, the recombinant expression vector is either a viral vector, e.g., a retroviral vector, or a non-viral vector, e.g., a transposon-based Sleeping Beauty vector. The recombinant expression vector comprises regulatory sequences, such as transcription and translation initiation and termination codons, which are specific to the type of host cell (e.g., bacterium, fungus, plant, or animal) into which the vector is to be introduced and in which the expression of the nucleic acid of the invention shall be performed. Furthermore, the vector of the invention may include one or more marker genes, which allow for selection of transformed or transfected hosts. The recombinant expression vector can comprise a native or normative promoter operably linked to the nucleotide sequence encoding the constructs of the invention, or to the nucleotide sequence which is complementary to or which hybridizes to the nucleotide sequence encoding the constructs of the invention. The selection of promoters include, e.g., strong, weak, inducible, tissue-specific and developmental-specific promoters. The promoter can be a non-viral promoter or a viral promoter. The inventive recombinant expression vectors can be designed for either transient expression, for stable expression, or for both. Also, the recombinant expression vectors can be made for constitutive expression or for inducible expression.

The invention also pertains to a host cell comprising an antigen recognizing construct in accordance with the invention. Specifically the host cell of the invention comprises a nucleic acid, or a vector as described herein above. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood leukocyte (PBL) or a peripheral blood mononuclear cell (PBMC). More preferably, the host cell is a T cell. The T cell can be any T cell, such as a cultured T cell, e.g., a primary T cell, or a T cell from a cultured T cell line, e.g., Jurkat, SupTl, etc., or a T cell obtained from a mammal, preferably a T cell or T cell precurser from a human patient. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. More preferably, the T cell is a T cell isolated from a human. The T cell can be any type of T cell and can be of any developmental stage, including but not limited to, CD4positive and/or CD8positive, CD4 positive helper T cells, e.g., Th1 and Th2 cells, CD8 positive T cells (e.g., cytotoxic T cells), tumor infiltrating cells (TILs), memory T cells, naive T cells, and the like. Preferably, the T cell is a CD8 positive T cell or a CD4 positive T cell.

Preferably, the host cell of the invention is a lymphocyte, preferably a T lymphocyte, such as a CD4 or CD8 positive T-cell. The host cell furthermore preferably is a tumor reactive T cell specific for MAGE-A1 expressing tumor cells.

One further aspect of the present invention relates to the herein disclosed antigen recognizing constructs, nucleic acids, vectors and/or host cell for use in medicine. The use in medicine in one preferred embodiment includes the use in the diagnosis, prevention and/or treatment of an infectious disease, preferably a HPV infection, or a proliferative disease, such as a malignant or benign tumor disease. The tumor disease is for example a HPV-associated cancer.

The constructs, proteins, TCRs antibodies, poylpeptides and nucleic acids of the invention are in particular for use in immune therapy, preferably in adoptive T cell therapy. The administration of the compounds of the invention can for example involve the infusion of T cells of the invention into said patient. Preferably such T cells are autologous T cells of the patient which were in vitro transduced with a nucleic acid or antigen recognizing constructs of the present invention.

The objective of the invention is also solved by a method for the manufacturing of an HPV specific antigen recognizing construct (ARC) expressing cell line, comprising
  a. Providing a suitable host cell,
  b. Providing a genetic construct encoding for an ARC, wherein said ARC comprises a CDR3 having an amino acid sequence with at least 50%, 60%, 70%, 80%, 90%, 95%, 98%, 99%, or 100% sequence identity to an amino acid sequence selected from SEQ ID Nos. 9 to 28,
  c. Introducing into said suitable host cell said genetic construct,
  d. Expressing said genetic construct by said suitable host cell.

The above method may in one preferred embodiment further comprise the step of including a cell surface presentation of said ARC.

Of course it is also preferred that context of this aspect of the invention said ARC is an ARC according to the inventive aspects as described herein above. In this respect it is also additionally or alternatively preferred that said ARC is of mammalian origin, preferably of human origin.

The preferred suitable host cell for use in the method of the invention is a mammalian, in particular a human cell, such as a human T-cell. T cells for use in the invention are described in detail herein above.

The ARC produced according to the method of the invention is in one embodiment a TCR. For example also included are TCRs with additional (functional) domains or a TCR provided with alternative domains, e.g. a TCR provided with a foreign transmembrane-domain as membrane anchor. A TCR produced in accordance with the present invention is for example an alpha/beta TCR, gamma/delta TCR or a single chain TCR (scTCR). Also, TCR forms which are included by the present invention are generally any TCR known in the art, specifically those described herein above.

Desirably, the transfection system for use in the method in accordance with the invention is a retroviral vector system. Such systems are well known to the skilled artisan.

Also comprised by the present invention is in one embodiment the additional method step of purification of the ARC from the cell and, optionally, the reconstitution of the translated ARC-fragments in a T-cell.

In an alternative aspect of the invention a T-cell is provided obtained or obtainable by a method for the production of a T cell receptor (TCR), which is specific for tumorous cells and has high avidity as described herein above. Such a T cell is depending on the host cell used in the method of the invention for example a human or non-human T-cell, preferably a human TCR.

The inventive TCRs, polypeptides, proteins, (including functional variants thereof), nucleic acids, recombinant expression vectors, host cells (including populations thereof), and antibodies (including antigen binding portions thereof), can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70%, 80%, 90%, 95%, or can be 100%.

The inventive antigen recognizing constructs, TCRs, polypeptides, proteins (including functional variants thereof), nucleic acids, recombinant expression vectors, host cells (including populations thereof), and antibodies (including antigen binding portions thereof), all of which are collectively referred to as "inventive TCR materials" hereinafter, can be formulated into a composition, such as a pharmaceutical composition. In this regard, the invention provides a pharmaceutical composition comprising any of the TCRs, polypeptides, proteins, functional portions, functional variants, nucleic acids, expression vectors, host cells (including populations thereof), and antibodies (including antigen binding portions thereof) described herein, and a pharmaceutically acceptable carrier. The inventive pharmaceutical compositions containing any of the inventive TCR materials can comprise more than one inventive TCR material, e.g., a polypeptide and a nucleic acid, or two or more different TCRs (including functional portions and functional variants thereof). Alternatively, the pharmaceutical composition can comprise an inventive TCR material in combination with another pharmaceutically active agent(s) or drug(s), such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. Preferably, the carrier is a pharmaceutically acceptable carrier. With respect to pharmaceutical compositions, the carrier can be any of those conventionally used for the particular inventive TCR material under consideration. Such pharmaceutically acceptable carriers are well-known to those skilled in the art and are readily available to the public. It is preferred that the pharmaceutically acceptable carrier be one which has no detrimental side effects or toxicity under the conditions of use.

Thus also provided is a pharmaceutical composition, comprising any of the herein described products of the invention, specifically any proteins, nucleic acids or host cells. In a preferred embodiment the pharmaceutical composition is for immune therapy.

Preferably, the inventive TCR material is administered by injection, e.g., intravenously. When the inventive TCR material is a host cell expressing the inventive TCR (or functional variant thereof), the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, Ill.), PLASMA-LYTE A (Baxter, Deerfield, Ill.), about 5% dextrose in water, or Ringer's lactate. In an embodiment, the pharmaceutically acceptable carrier is supplemented with human serum albumen.

For purposes of the invention, the amount or dose (e.g., numbers of cells when the inventive TCR material is one or more cells) of the inventive TCR material administered should be sufficient to effect, e.g., a therapeutic or prophylactic response, in the subject or animal over a reasonable time frame. For example, the dose of the inventive TCR material should be sufficient to bind to a cancer antigen, or detect, treat or prevent cancer in a period of from about 2 hours or longer, e.g., 12 to 24 or more hours, from the time of administration. In certain embodiments, the time period could be even longer. The dose will be determined by the efficacy of the particular inventive TCR material and the condition of the animal (e.g., human), as well as the body weight of the animal (e.g., human) to be treated.

It is contemplated that the inventive pharmaceutical compositions, TCRs (including functional variants thereof), polypeptides, proteins, nucleic acids, recombinant expression vectors, host cells, or populations of cells can be used in methods of treating or preventing cancer, HPV infection, or HPV-positive premalignancy. Without being bound to a particular theory, the inventive TCRs (and functional variants thereof) are believed to bind specifically to HPV antigen, such that the TCR (or related inventive polypeptide or protein and functional variants thereof), when expressed by a cell, is able to mediate an immune response against a target cell expressing HPV antigens of the invention. In this regard, the invention provides a method of treating or preventing a condition in a mammal, comprising administering to the mammal any of the pharmaceutical compositions, TCRs (and functional variants thereof), polypeptides, or proteins described herein, any nucleic acid or recombinant expression vector comprising a nucleotide sequence encoding any of the TCRs (and functional variants thereof), polypeptides, proteins described herein, or any host cell or population of cells comprising a recombinant vector which encodes any of the TCRs (and functional variants thereof), polypeptides, or proteins described herein, in an amount effective to treat or prevent the condition in the mammal, wherein the condition is cancer, HPV infection, or HPV-positive premalignancy.

Examples of pharmaceutically acceptable carriers or diluents useful in the present invention include stabilizers such as SPGA, carbohydrates (e.g. sorbitol, mannitol, starch, sucrose, glucose, dextran), proteins such as albumin or casein, protein containing agents such as bovine serum or skimmed milk and buffers (e.g. phosphate buffer).

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of a condition in a mammal. Furthermore, the treatment or prevention provided by the inventive method can include treatment or prevention of one or more conditions or symptoms of the condition, e.g., cancer, being treated or prevented. For example, treatment or prevention can include promoting the regression of a tumor. Also, for purposes herein, "prevention" can encompass delaying the onset of the condition, or a symptom or condition thereof.

Also provided is a method of detecting the presence of a condition in a mammal. The method comprises (i) contacting a sample comprising one or more cells from the mammal with any of the inventive TCRs (and functional variants thereof), polypeptides, proteins, nucleic acids, recombinant expression vectors, host cells, populations of cells, antibodies, or antigen binding portions thereof, or pharmaceutical compositions described herein, thereby forming a complex, and detecting the complex, wherein detection of the complex is indicative of the presence of the condition in the mammal, wherein the condition is cancer, HPV 16 infection, or HPV-positive premalignancy.

With respect to the inventive method of detecting a condition in a mammal, the sample of cells can be a sample comprising whole cells, lysates thereof, or a fraction of the whole cell lysates, e.g., a nuclear or cytoplasmic fraction, a whole protein fraction, or a nucleic acid fraction.

For purposes of the inventive detecting method, the contacting can take place in vitro or in vivo with respect to the mammal. Preferably, the contacting is in vitro.

Also, detection of the complex can occur through any number of ways known in the art. For instance, the inventive TCRs (and functional variants thereof), polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

For purposes of the inventive methods, wherein host cells or populations of cells are administered, the cells can be cells that are allogeneic or autologous to the mammal. Preferably, the cells are autologous to the mammal.

With respect to the above mentioned medical applications of the TCR material of the invention, the to be treated and/or diagnosed cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, chronic lymphocytic leukemia, chronic myeloid cancer, colon cancer, esophageal cancer, cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, and urinary bladder cancer. A preferred cancer is cancer is cancer of the uterine cervix, oropharynx, anus, anal canal, anorectum, vagina, vulva, or penis. A particularly preferred cancer is HPV positive cancer, such as a HPV 16 or HPV 18 positive cancer. While the cancers most commonly associated with HPV 16/18 infection include cancer of the uterine cervix, oropharynx, anus, anal canal, anorectum, vagina, vulva, and penis, the inventive methods may be used to treat any HPV-positive cancer, including those that occur at other anatomical areas.

In general the invention provides a method for treating a subject suffering from a tumor or tumor disease comprising the administration of the antigen recognizing constructs, nucleic acids, vectors and/or host cell as disclosed by the present invention. Preferably the subject is a subject in need of such a treatment. The subject in preferred embodiments is a mammalian subject, preferably a human patient, suffering from a tumor or tumor disease, which is HPV positive.

The present invention will now be further described in the following examples with reference to the accompanying figures and sequences, nevertheless, without being limited thereto. For the purposes of the present invention, all references as cited herein are incorporated by reference in their entireties. In the Figures and Sequences:

FIG. 1: shows examples for the specific CD8+ T cell response against HLA-A*02.01 restricted HPV16 E6 epitope TIHDIILECV in ABabDII mice. ABabDII mice were either immunized i.p. with E6/7 expressing adenovirus followed by s.c. administration of 50 µg of E6 peptide together with 50 µg of CpG ODN 1826 emulsified in IFA, or with peptide/CpG/IFA mixture alone. The presence of HPV-specific CD8+ T cells in the peripheral blood of immunized animals was assessed by intracellular IFNγ staining 7 days after each boost. Stimulation with phorbol myristate acetate (PMA) and ionomycin was used as a positive control (+ctrl).

Figure 2:
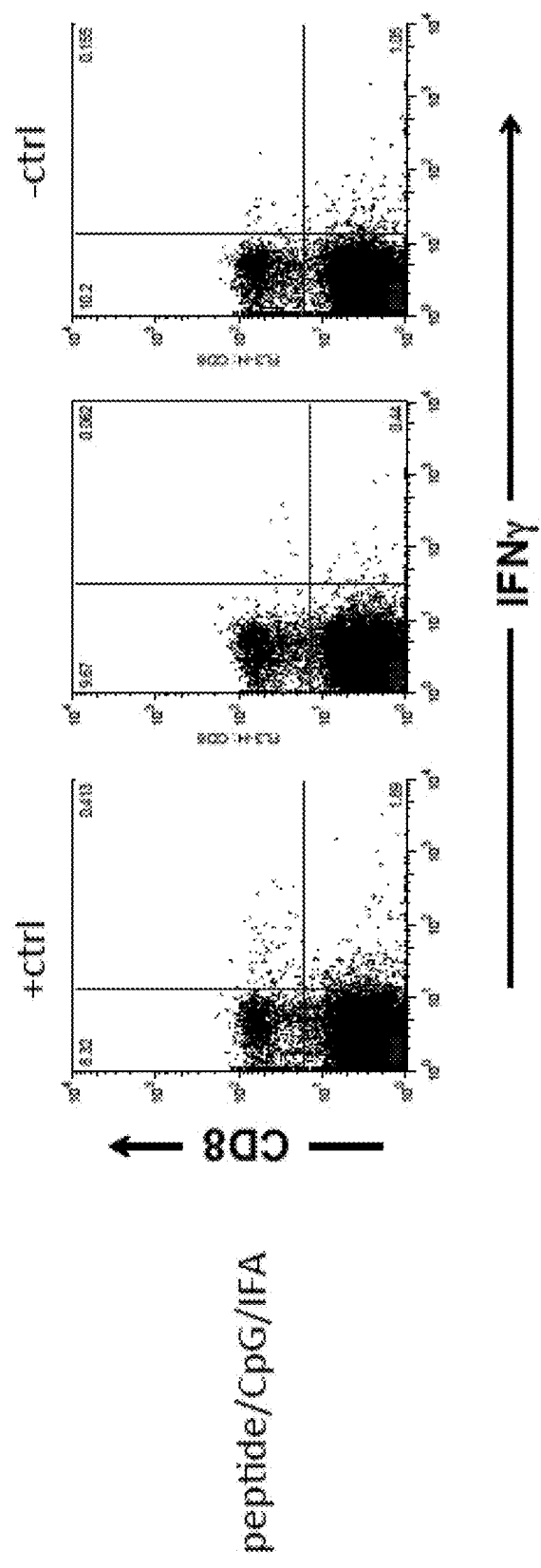

FIG. 2: shows an example for the specific CD8+ T cell response against HLA-A201 restricted HPV16 E7 epitope TLGIVCPI in ABabDII mice. ABabDII mice were immunized s.c. at the tail base with 50 µg of E7 peptide together with 50 µg of CpG ODN 1826 emulsified in IFA. The presence of HPV-specific CD8+ T cells in the peripheral blood of immunized animals was assessed by intracellular IFNγ staining 7 days after each boost. Stimulation with phorbol myristate acetate (PMA) and ionomycin was used as a positive control (+ctrl).

Figure 3:
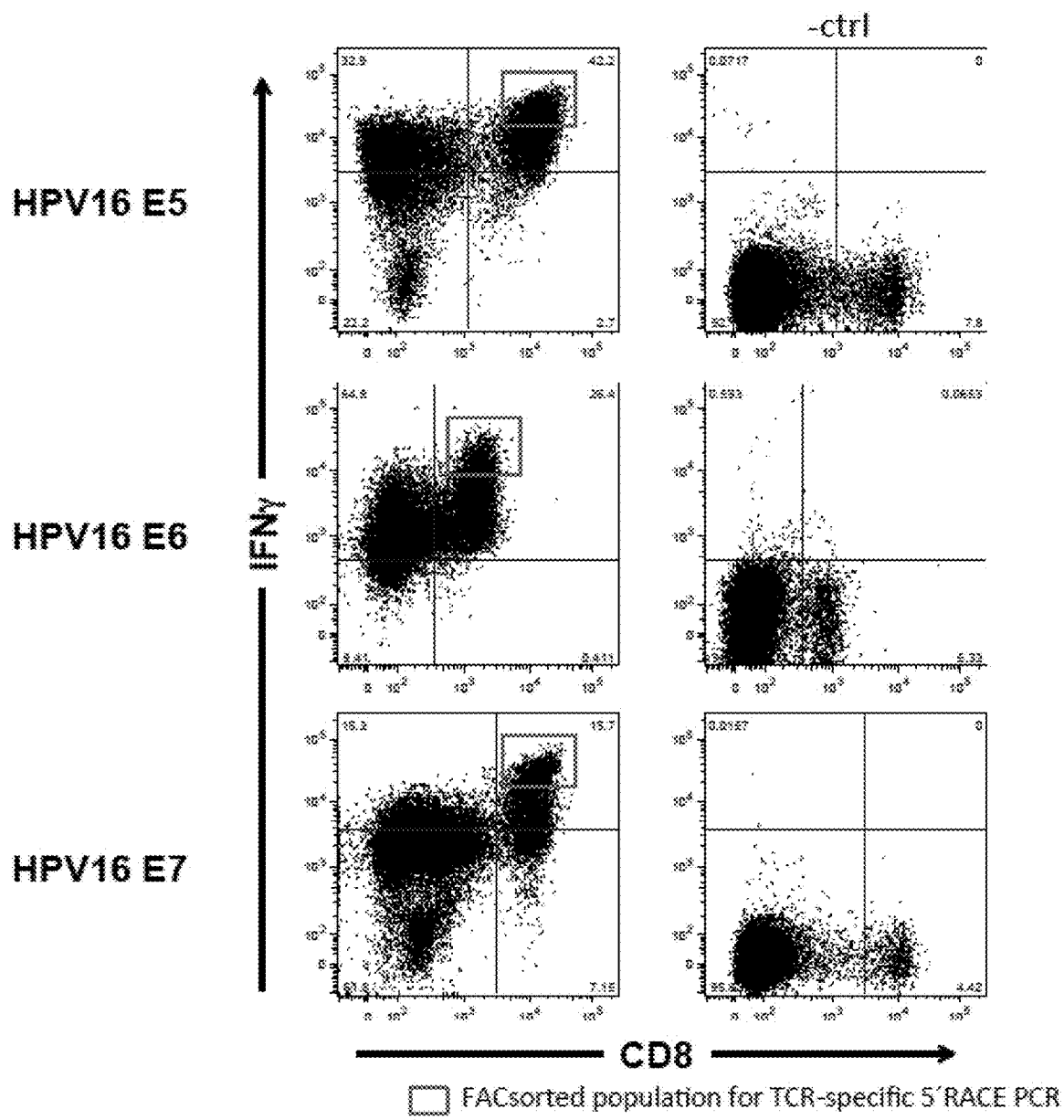

FIG. 3: shows FACSort strategy (IFNγ capture assay) for the specific CD8+ T cells against HLA-A*02.01 restricted HPV16 E5, E6 and E7 epitopes. Spleen cells from responsive mice were depleted for CD4+ T cells and restimulated for 10 days with $10^{-8}$ mol of the respective peptide. For 5'RACE PCR HPV-specific CD8+ T cells were sorted directly into RNA purification buffer using IFNγ capture assay.

Figure 4:
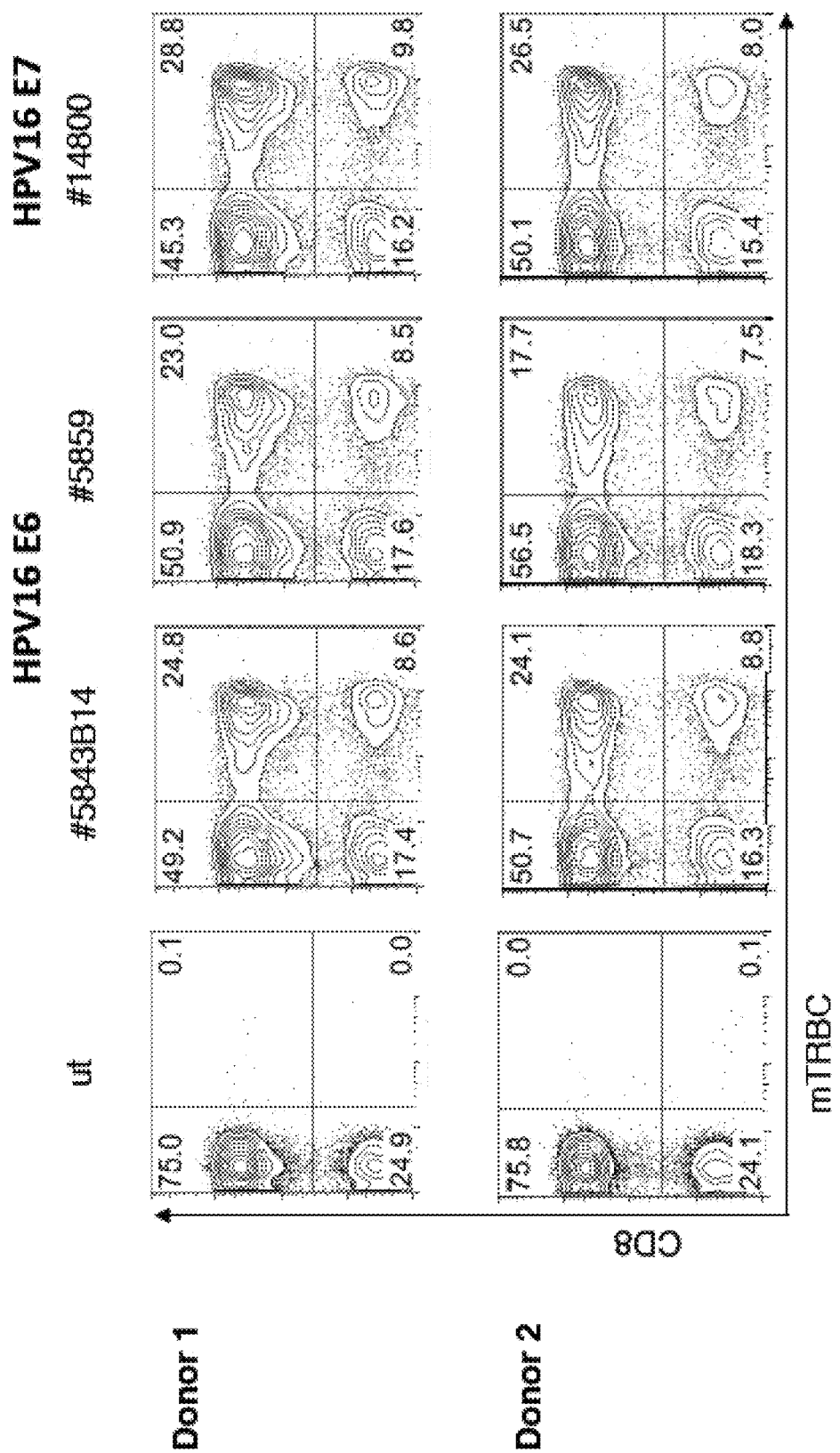

FIG. 4: shows HPV16 E6 and E7 TCR transduction of freshly prepared human PBLs. $1\times10^6$ freshly isolated or frozen hPBMCs were stimulated with anti-CD3 and anti-CD28-coated plates in the presence of 200 U/ml recombinant human interleukin 2. Transductions were done 48 and 72 h after stimulation by addition of retrovirus containing supernatant and protamine sulfate followed by spinoculation ($1^{st}$ transduction) or preloading of virus onto retronectin (Takara)-coated plates and spinoculation ($2^{nd}$ transduction). Transduction efficacy was assessed by staining with anti-CD8 and anti-mouse constant TCRβ mAbs.

Figure 5:
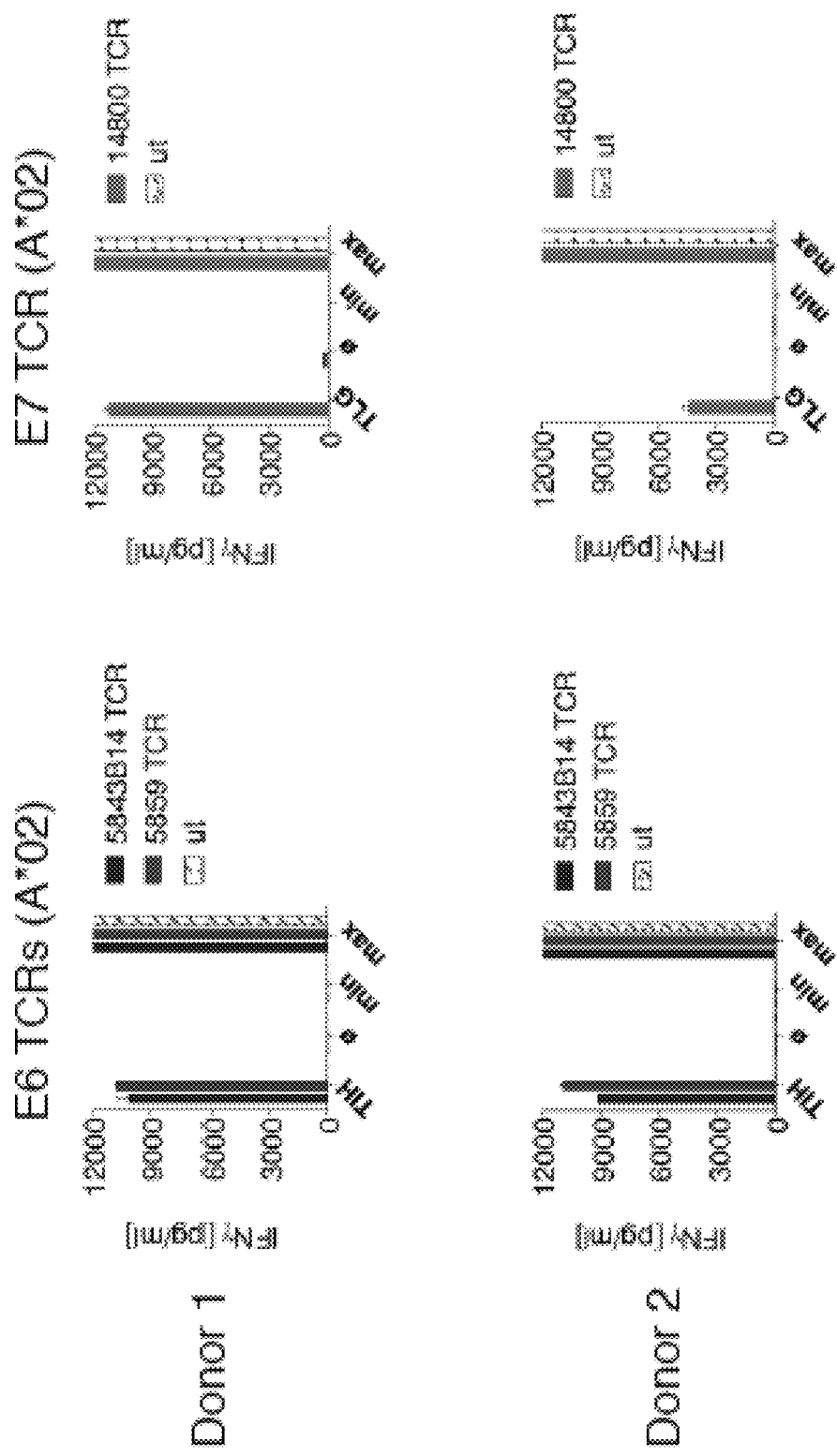

FIG. 5: shows the HPV16 E6/E7 peptide-specific IFN-γ release of TCR transduced human PBMCs; 5859 TCR corresponds to Seq ID No: 34 & 35, 5843B14 TCR corresponds to Seq ID No: 36 & 37, 14800 TCR corresponds to Seq ID NO: 43&44. IFNγ production was measured by enzyme-linked immunosorbent assay after 16 h coculture of $1\times10^4$ TCR-transduced T cells with $1\times10^4$ peptide-loaded T2 cells. Stimulation with phorbol myristate acetate (PMA) and ionomycin was used as a positive control (max); ut=untransduced PBMCs.

Figure 6:
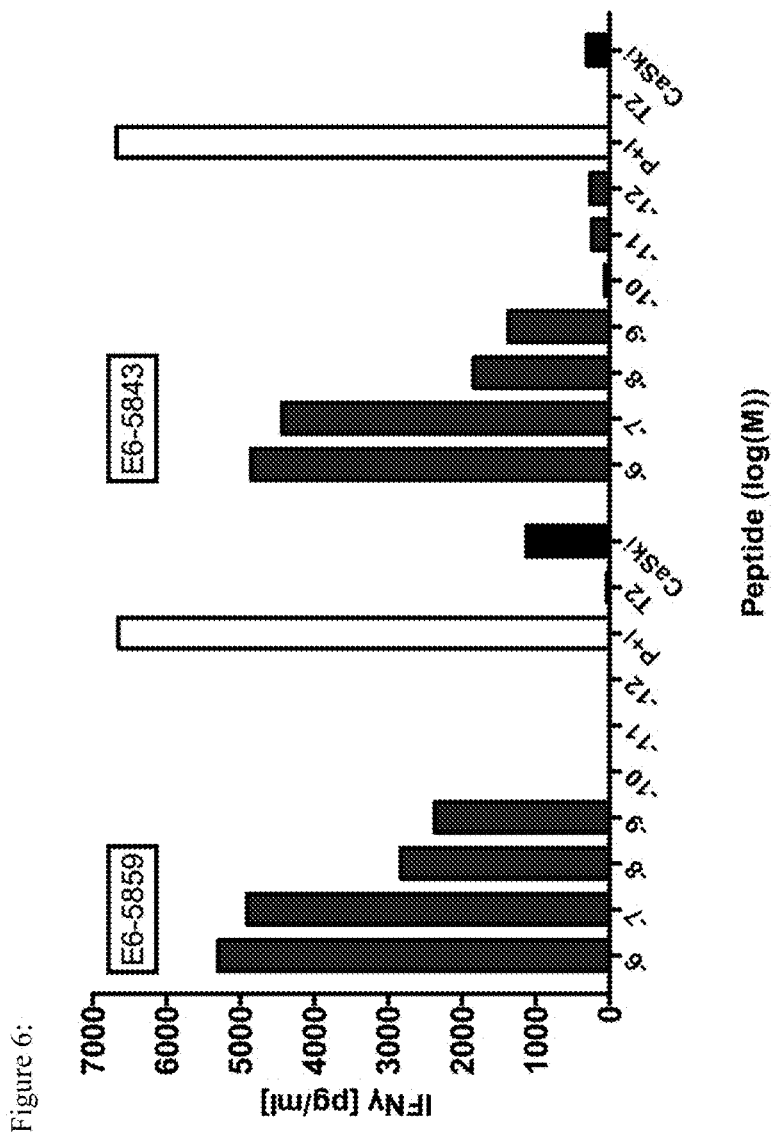

FIG. 6: shows the HPV16 E6 IFN-γ release of TCR transduced human PBMCs on titrated E6-specific peptide and CASKI cell line. Left panel shows the TCR of SEQ ID NO 14/15 (T3), right panel shows TCR of SEQ ID NO 16/17 (T4). IFNγ production was measured by enzyme-linked immunosorbent assay after 16 h coculture of $1\times10^4$ TCR-transduced T cells with $1\times10^4$ peptide-loaded T2 cells or $1\times10^4$ cells of CASKI cell line. Stimulation with phorbol myristate acetate (PMA) and ionomycin was used as a positive control (P+I). IFNγ release comparable to recognition of CASKI cells was also seen for HLA-transduced cervical cancer cell lines SiHa cell line and head and neck cancer cell lines SCC-090 and SCC-152 (not shown).

Figure 7:
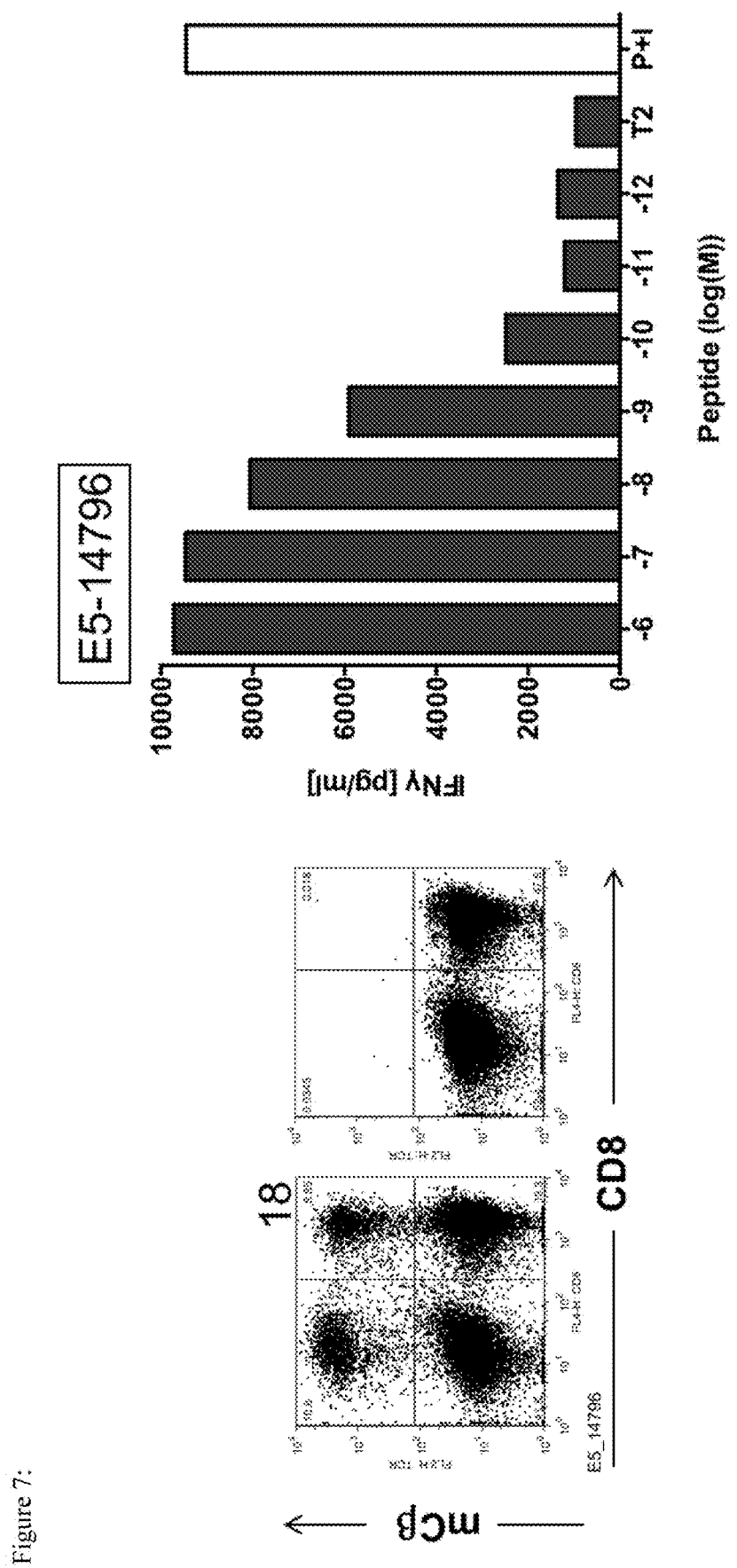

FIG. 7: shows the HPV16 E5 transduction of freshly prepared human PBLs and HPV16 E5 peptide-specific IFN-γ release of TCR transduced human PBMCs. TCR used was the TCR of SEQ ID NO 12/13 (T2). 1×10⁶ freshly isolated or frozen hPBMCs were stimulated with anti-CD3 and anti-CD28-coated plates in the presence of 200 U/ml recombinant human interleukin 2. Transductions were done 48 and 72 h after stimulation by addition of retrovirus containing supernatant and protamine sulfate followed by spinoculation (1$^{st}$ transduction) or preloading of virus onto retronectin (Takara)-coated plates and spinoculation (2$^{nd}$ transduction). Transduction efficacy was assessed by staining with anti-CD8 and anti-mouse constant TCRβ mAbs. IFNγ production was measured by enzyme-linked immunosorbent assay after 16 h coculture of 1×10⁴ TCR-transduced T cells with 1×10⁴ peptide-loaded T2 cells. Stimulation with phorbol myristate acetate (PMA) and ionomycin was used as a positive control (P+I).

SEQ ID No 1 to 8: show the HPV 16 and 18 epitopes that are bound by the TCR of the invention.

SEQ ID No 9 to 28: show alpha and beta chain CDR3 sequences of the TCR of the invention.

SEQ ID No 29 to 48: show the full variable sequences of α and β chains of the TCR of the present invention.

EXAMPLES

HPV Epitopes used for Immunization of Animals:

TABLE 1

| HPV Gene | Protein | HLA A2.01 Epitope | SEQ ID NO: |
|---|---|---|---|
| 16-E5 | Human papillomavirus type 16 E5 protein | YIIFVYIPL (63-71) | 1 |
| 16-E6 | Human papillomavirus type 16 E6 protein | KLPQLCTEL (11-19) | 2 |
| 16-E6 | Human papillomavirus type 16 E6 protein | TIHDIILECV (29-38) | 3 |
| 16-E7 | Human papillomavirus type 16 E7 protein | YMLDLQPET (86-93) | 4 |
| 16-E7 | Human papillomavirus type 16 E7 protein | YMLDLQPETT (11-20) | 5 |
| 16-E7 | Human papillomavirus type 16 E7 protein | TLGIVCPI (86-93) | 6 |
| 18-E6 | Human papillomavirus type 18 E6 protein | KCIDFYSRI (67-75) | 7 |
| 18-E7 | Human papillomavirus type 18 E7 protein | FQQLFLNTL (86-94) | 8 |

Peptide Epitopes with CTL reactivity in ABabDII mice

Example 1: T-Cell Receptor T1 Recognizing HPV 16-E5 Epitope YIIFVYIPL

| TCR | Antigen | Immunogenic peptide/ purification | TCR sequence | CDR3 SEQ ID NO: |
|---|---|---|---|---|
| T1* | E5 | YIIFVYIPL | TRAV13-1*01-CAASSYNQGGKLF-TRAJ23*-1 | 9 |
| | | IFNγ-CAPTURE | TRAV26-2*01-CILRDVNAGGTSYGKLTF-TRAJ52*01 | 10 |
| | | | TRBV12-3*01-CASSLLSSYNEQFF-TRBD2*01-TRBJ2-3*01 | 11 |

CDR1 sequences are bold
CDR2 sequences are double underlined
CDR3 sequences are underlined
Full length variable chain sequences (CDR3 sequences are underlined):

TRAV13-1*01-CAASSYNQGGKLIF-TRAJ23*01

(SEQ ID NO: 29)
MTSIRAVF IFLWLQLDLV NGENVEQHPS TLSVQEGDSA VIKCTYSDSA SNYFPWYKQE LGKGPQLIID

IRSNVGEKKD QRIAVTLNKT AKHFSLHITE TQPEDSAVYF CAASSYNQGG KLIFGQGTEL SVKPN

TRAV26-2*01-CILRDVNAGGTSYGKLTF-TRAJ52*01

-continued (SEQ ID NO: 30)
MKLVTSIT VLLSLGIMGD AKTTQPNSME SNEEEPVHLP CNHSTISGTD YIHWYRQLPS QGPEYVIH<u>GL TSN</u>VNNRMAS LAIAEDRKSS TLILHRATLR DAAVYY<u>CILR DVNAGGTSYG KLTF</u>GQGTIL

TVHPN

TRBV12-3*01-CASSLLSSYNEQFF-TRBD2*01-TRBJ2-3*01
(SEQ ID NO: 31)
MDSWTF CCVSLCILVA KHTDAGVIQS PRHEVTEMGQ EVTLRCKPIS GHNSLFWYRQ TMMRGLELLI

Y<u>FNNNVP</u>IDD SGMPEDRFSA KMPNASFSTL KIQPSEPRDS AVYF<u>CASSLL SSYNEQFF</u>GP GTRLTVL

Example 2: T-Cell Receptor T2 Recognizing HPV 16-E5 Epitope YIIFVYIPL

| TCR | Antigen | Immunogenic peptide/ purification | TCR sequence | CDR3 SEQ ID NO: |
|---|---|---|---|---|
| T2 | E5 | YIIFVYIPL | TRAV12-2*02-CAVNVDFNKFYF-TRAJ21*01 | 12 |
| | | IFNγ-CAPTURE | TRBV4-1*01-CASSQDWNNEQFF-TRBD1*01-TRBJ2-1*01 | 13 |

Full length variable chain sequences (CDR3 sequences are underlined):

TRAV12-2*02-CAVNVDFNKFYF-TRAJ21*01
(SEQ ID NO): 32:
MMKSLRVLLV ILWLQLSWVW SQQKEVEQNS GPLSVPEGAI

ASLNCTYS<u>DR GSQS</u>FFWYRQ YSGKSPELIM <u>SIYSNGD</u>KED

GRFTAQLNKA SQYVSLLIRD SQPSDSATYL <u>CAVNVDFNKF</u>

<u>YF</u>GSGTKLNV KPN

TRBV4-1*01-CASSQDWNNEQFF-TRBD1*01-TRBJ2-1*01
SEQ ID NO: 33:
MGCRLL CCAVLCLLGA VPIDTEVTQT PKHLVMGMTN

KKSLKCEQHM GHRAMYWYKQ KAKKPPELMF V<u>YSYEKL</u>SIN

ESVPSRFSPE CPNSSLLNLH LHALQPEDSA LYL<u>CASSQDW</u>

<u>NNEQFF</u>GPGT RLTVL

Example 3: T-Cell Receptor T3 Recognizing HPV 16-E6 Epitope TIHDIILECV

| TCR | Antigen | Immunogenic peptide/ purification | TCR sequence | CDR3 SEQ ID NO: |
|---|---|---|---|---|
| T3 | E6 | TIHDIILECV | TRAV20*02-CAVQANRGSTLGRLYF-TRAJ18*01 | 14 |
| | | IFNγ-CAPTURE | TRBV28*01-CASSLWGRLAKNIQYF-TRBD1*01-TRBJ2-4*01 | 15 |

Full length variable chain sequences (CDR3 sequences are underlined):

TRAV20*02-CAVQANRGSTLGRLYF-TRAJ18*01
SEQ ID NO: 34
MEKMLEC AFIVLWLQLG WLSGEDQVTQ SPEALRLQEG

ESSSLNCSYT VSGLRGLFWY RQDPGKGPEF LFT<u>LYSAGEE</u>

KEKERLKATL TKKESFLHIT APKPEDSATY L<u>CAVQANRGS</u>

<u>TLGRLYF</u>GRG TQLTVWPD

TRBV28*01-CASSLWGRLAKNIQYF-TRBD1*01-TRBJ2-4*01
SEQ ID NO: 35
MGIRLL CRVAFCFLAV GLVDVKVTQS SRYLVKRTGE

KVFLECVQDM DHENMFWYRQ DPGLGLRLIY F<u>SYDVKM</u>KEK

GDIPEGYSVS REKKERFSLI LESASTNQTS MYL<u>CASSLWG</u>

<u>RLAKNIQYF</u>G AGTRLSVL

Example 4: T-Cell Receptor T4 Recognizing HPV 16-E6 Epitope TIHDIILECV

| TCR | Antigen | Immunogenic peptide/ purification | TCR sequence | CDR3 SEQ ID NO: |
|---|---|---|---|---|
| T4 | E6 | TIHDIILECV | TRAV21*02-CAVRETSGSRLTF-TRAJ58*01 | 16 |
| | | IFNγ-CAPTURE | TRBV28*01-CASSFWGRSTDTQYF-TRBD1*01-TRBJ2-3*01 | 17 |

Full length variable chain sequences (CDR3 sequences are underlined):

TRAV21*02-CAVRETSGSRLTF-TRAJ58*01
SEQ ID NO: 36
METLLGLL ILWLQLQWVS SKQEVTQIPA ALSVPEGENL

VLNCSFTDSA IYNLQWFRQD PGKGLTSLLL <u>IQSSQREQTS</u>

-continued

GRLNASLDKS SGRSTLYIAA SQPGDSATYL CAVRETSGSR

LTFGEGTQLT VNPD

TRBV28*01-CASSFWGRSTDTQYF-TRBD1*01-TRBJ2-3*01
SEQ ID NO: 37
MGIRLL CRVAFCFLAV GLVDVKVTQS SRYLVKRTGE

KVFLECVQDM DHENMFWYRQ DPGLGLRLIY FSYDVKMKEK

GDIPEGYSVS REKKERFSLI LESASTNQTS MYLCASSFWG

RSTDTQYFGP GTRLTVL

Example 5: T-Cell Receptor T5 Recognizing HPV 16-E6 Epitope TIHDIILECV

| TCR | Antigen | Immunogenic peptide/ purification | TCR sequence | CDR3 SEQ ID NO: |
|---|---|---|---|---|
| T5* | E6 | TIHDIILECV | TRAV17*01-CATVSTDSWGKKLQF-TRAJ24*02 | 18 |
| | | IFNγ-CAPTURE | TRBV10-3*02-CAISDSNGINIQYF-TRBD2*02-TRBJ2-4*01 | 19 |
| | | | TRBV28*01-CASSLWGRAGKDTQYF-TRBD2*02-TRBJ2-3*01 | 20 |

Full length variable chain sequences (CDR3 sequences are underlined):

TRAV17*01-CATVSTDSWGKKLQF-TRAJ24*02
SEQ ID NO: 38
M ETLLGVSLVI LWLQLARVNS QQGEEDPQAL

SIQEGENATM NCSYKTSINN LQWYRQNSGR GLVHLILIRS

NEREKHSGRL RVTLDTSKKS SSLLITASRA ADTASYFCAT

VSTDSWGKLQ FGAGTQVVVT PD

TRBV10-3*02-CAISDSNGINIQYF-TRBD2*02-TRBJ2-4*01
SEQ ID NO: 39
MRSWPG PEMGTRLFFY VALCLLWTGH MDAGITQSPR

HKVTETGTPV TLRCHQTENH RYMYWYRQDP GHGLRLIHYS

YGVKDTDKGE VSDGYSVSRS KTEDFLLTLE SATSSQTSVY

FCAISDSNGI NIQYFGAGTR LSVL

TRBV28*01-CASSLWGRAGKDTQYF-TRBD2*02-TRBJ2-3*01
SEQ ID NO: 40
MGIRLL CRVAFCFLAV GLVDVKVTQS SRYLVKRTGE

KVFLECVQDM DHENMFWYRQ DPGLGLRLIY FSYDVKMKEK

GDIPEGYSVS REKKERFSLI LESASTNQTS MYLCASSLWG

RAGKDTQYFG PGTRLTVL

Example 6: T-Cell Receptor T6 Recognizing HPV 16-E6 Epitope KLPQLCTEL

| TCR | Antigen | Immunogenic peptide/ purification | TCR sequence | CDR3 SEQ ID NO: |
|---|---|---|---|---|
| T6 | E6 | KLPQLCTEL | TRAV8-6*01-CAVSLNSGNTPLVF-TRAJ29*01 | 21 |
| | | IFNγ-CAPTURE | TRBV20-1*01-CSARDLAGNTGELFF-TRBD2*01-TRBJ2-2*01 | 22 |

Full length variable chain sequences (CDR3 sequences are underlined):

TRAV8-6*01-CAVSLNSGNTPLVF-TRAJ29*01
SEQ ID NO: 41
ML LLLVPAFQVI FTLGGTRAQS VTQLDSQVPV

FEEAPVELRC NYSSSVSVYL FWYVQYPNQG LQLLLKYLSG

STLVESINGF EAEFNKSQTS FHLRKPSVHI SDTAEYFCAV

SLNSGNTPLV FGKGTRLSVI AN

TRBV20-1*01-CSARDLAGNTGELFF-TRBD2*01-TRBJ2-2*01
SEQ ID NO: 42
MLLLLLLLGP GSGLGAVVSQ HPSWVICKSG TSVKIECRSL

DFQATTMFWY RQFPKQSLML MATSNEGSKA TYEQGVEKDK

FLINHASLTL STLTVTSAHP EDSSFYICSA RDLAGNTGEL

FFGEGSRLTVL

Example 7: T-Cell Receptor T7 Recognizing HPV 16-E7 Epitope TLGIVCPI

| TCR | Antigen | Immunogenic peptide/ purification | TCR sequence | CDR3 SEQ ID NO: |
|---|---|---|---|---|
| T7 | E7 | TLGIVCPI | TRAV30*01-CGTGTDSWGKLQF-TRAJ24*02 | 23 |
| | | IFNγ-CAPTURE | TRBV12-4*01-CASSPGLAGGEQFF-TRBD2*02-TRBJ2-1*01 | 24 |

Full length variable chain sequences (CDR3 sequences are underlined):

TRAV30*01-CGTGTDSWGKLQF-TRAJ24*02
SEQ ID NO: 43
METLLKVL SGTLLWQLTW VRSQQPVQSP QAVILREGED

AVINCSSSKA LYSVHWYRQK HGEAPVFLMI LLKGGEQKGH

EKISASFNEK KQQSSLYLTA SQLSYSGTYF CGTGTDSWGK

LQFGAGTQVV VTPD

TRBV12-4*01-CASSPGLAGGEQFF-TRBD2*02-TRBJ2-1*01
SEQ ID NO: 44

MGSWTL CCVSLCILVA KHTDAGVIQS PRHEVTEMGQ

EVTLRCKPIS GHDYLFWYRQ TMMRGLELLI <u>YFNNNVP</u>IDD

SGMPEDRFSA KMPNASFSTL KIQPSEPRDS AVYF<u>CASSPG</u>

<u>LAGGEQFFGP</u> GTRLTVL

Example 8: T-Cell Receptor T8 Recognizing HPV 16-E7 Epitope TLGIVCPI

| TCR | Antigen | Immunogenic peptide/ purification | TCR sequence | CDR3 SEQ ID NO: |
|---|---|---|---|---|
| T8 | E7 | TLGIVCPI | TRAV22*01-CAVEPNSGNTPLVF-TRAJ29*01 | 25 |
|  |  | IFNγ-CAPTURE | TRBV7-2*02 or 03-CASSLIISYNEQFF-TRBJ2-1*01 | 26 |

Full length variable chain sequences (CDR3 sequences are underlined):

TRAV22*01-CAVEPNSGNTPLVF-TRAJ29*01
SEQ ID NO: 45
MKRILGAL LGLLSAQVCC VRGIQVEQSP PDLILQEGAN

STLRCNFSDS VNNLQWFHQN PWGQLINLFY <u>IPSGTKQNGR</u>

LSATTVATER YSLLYISSSQ TTDSGVYF<u>CA VEPNSGNTPL</u>

<u>VF</u>GKGTRLSV IAN

TRBV7-2*02 or 03-CASSLIISYNEQFF-TRBJ2-1*01
SEQ ID NO: 46
MGTRLL FWVAFCLLGA YHTGAGVSQS PSNKVTEKGK

DVELRCDPIS GHTALYWYRQ RLGQGLEFLI <u>YFQGNSA</u>PDK

SGLPSDRFSA ERTGESVSTL TIQRTQQEDS AVYL<u>CASSLI</u>

<u>ISYNEQFF</u>GP GTRLTVL

Example 9: T-Cell Receptor T9 Recognizing HPV 16-E7 Epitope TLGIVCPI

| TCR | Antigen | Immunogenic peptide/ purification | TCR sequence | CDR3 SEQ ID NO: |
|---|---|---|---|---|
| T9 | E7 | TLGIVCPI | TRAV38-2/DV-8*01-CAYRSAPYSGAGSYQLTF-TRAJ28*01 | 27 |
|  |  | IFNγ-CAPTURE | TRBV4-2*01-CASSQAPGLAGAEQYF-TRBD2*02-TRBJ2-7*01 | 28 |

Full length variable chain sequences (CDR3 sequences are underlined):

TRAV38-2/DV-8*01-CAYRSAPYSGAGSYQLTF-TRAJ28*01
SEQ ID NO: 47
MACPGFL WALVISTCLE FSMAQTVTQS QPEMSVQEAE

TVTLSCTYDT SESDYYLFWY KQPPSRQMIL VIR<u>QEAYKQQ</u>

<u>N</u>ATENRFSVN FQKAAKSFSL KISDSQLGDA AMYF<u>CAYRSA</u>

<u>PYSGAGSYQL TF</u>GKGTKLSV IPN

TRBV4-2*01-CASSQAPGLAGAEQYF-TRBD2*02-TRBJ2-7*01
SEQ ID NO: 48
MGCRLL CCAVLCLLGA VPMETGVTQT PRHLVMGMTN

KKSLKCEQHL GHNAMYWYKQ SAKKPLELMF <u>VYNFKEQTEN</u>

NSVPSRFSPE CPNSSHLFLH LHTLQPEDSA LYL<u>CASSQAP</u>

<u>GLAGAEQYFG</u> PGTRLTVT

Example 10: Interferon γ Release by TCR T2, T3 and T4 Transduced Cell Lines

FIGS. 6 and 7 show that T-cell lines transduced with the TCR T3 and T4 (FIG. 6) and T2 (FIG. 7). Results are shown in the figures and figure legend.

The invention claimed is:

1. An antigen recognizing construct comprising a T cell receptor (TCR), or an antigen binding fragment thereof, wherein the TCR or the antigen binding fragment thereof is composed of a TCR α chain sequence and a TCR β chain sequence, wherein
   (i) the TCR α chain sequence comprises an α chain complementary determining region 3 (CDR3), wherein an amino acid sequence of the α chain CDR3 comprises only one sequence selected from the group consisting of SEQ ID Nos: 9, 10, 12, 14, 16, 18, 21, 23, 25, and 27, and
   (ii) the TCR β chain sequence comprises a β chain CDR3; wherein an amino acid sequence of the β chain CDR3 comprises only one sequence selected from the group consisting of SEQ ID Nos: 11, 13, 15, 17, 19, 20, 22, 24, 26, and 28.

2. The antigen recognizing construct according to claim 1, wherein said TCR comprises a CDR1 and a CDR2 having sequences as set forth in SEQ ID NOs: 29 and 31; or 30 and 31; or 32 and 33; or 34 and 35; or 36 and 37; or 38 and 39; or 38 and 40; or 41 and 42; or 43 and 44; or 45 and 46; or 47 and 48.

3. The antigen recognizing construct according to claim 1, wherein said TCR comprises variable sequences as set forth in SEQ ID NOs: 29 and 31; or 30 and 31; or 32 and 33; or 34 and 35; or 36 and 37; or 38 and 39; or 38 and 40; or 41 and 42; or 43 and 44; or 45 and 46; or 47 and 48.

4. A nucleic acid encoding for an antigen recognizing construct according to claim 1.

5. A vector comprising a nucleic acid according to claim 4.

6. An isolated host cell comprising an antigen recognizing construct according to claim 1.

7. The host cell according to claim 6, comprising a lymphocyte.

8. An isolated host cell comprising a nucleic acid according to claim 4.

9. An isolated host cell comprising a vector according to claim 5.

10. The antigen recognizing construct according to claim 1, wherein the amino acid sequence of the α chain CDR3 consists of SEQ ID No. 9 or 10, and wherein the amino acid sequence of the β chain CDR consists of SEQ ID No. 11.

11. The antigen recognizing construct according to claim 1, wherein the amino acid sequence of the α chain CDR3 consists of SEQ ID No. 12, and wherein the amino acid sequence of the β chain CDR consists of SEQ ID No. 13.

12. The antigen recognizing construct according to claim 1, wherein the amino acid sequence of the α chain CDR3 consists of SEQ ID No. 14, and wherein the amino acid sequence of the β chain CDR consists of SEQ ID No. 15.

13. The antigen recognizing construct according to claim 1, wherein the amino acid sequence of the α chain CDR3 consists of SEQ ID No. 16, and wherein the amino acid sequence of the β chain CDR consists of SEQ ID No. 17.

14. The antigen recognizing construct according to claim 1, wherein the amino acid sequence of the α chain CDR3 consists of SEQ ID No. 18, and wherein the amino acid sequence of the β chain CDR consists of SEQ ID No. 20.

15. The antigen recognizing construct according to claim 1, wherein the amino acid sequence of the α chain CDR3 consists of SEQ ID No. 21, and wherein the amino acid sequence of the β chain CDR consists of SEQ ID No. 22.

16. The antigen recognizing construct according to claim 1, wherein the amino acid sequence of the α chain CDR3 consists of SEQ ID No. 23, and wherein the amino acid sequence of the β chain CDR consists of SEQ ID No. 24.

17. The antigen recognizing construct according to claim 1, wherein the amino acid sequence of the α chain CDR3 consists of SEQ ID No. 25, and wherein the amino acid sequence of the β chain CDR consists of SEQ ID No. 26.

18. The antigen recognizing construct according to claim 1, wherein the amino acid sequence of the α chain CDR3 consists of SEQ ID No. 27, and wherein the amino acid sequence of the β chain CDR consists of SEQ ID No. 28.

19. The antigen recognizing construct according to claim 1, wherein the amino acid sequence of the α chain CDR3 consists of SEQ ID No, 19, and wherein the amino acid sequence of the β chain CDR consists of SEQ ID No. 20.

* * * * *

SEQUENCE LISTING

<160> NUMBER OF SEQ ID NOS: 48

<210> SEQ ID NO 1
<211> LENGTH: 9
<212> TYPE: PRT
<213> ORGANISM: Human papillomavirus

<400> SEQUENCE: 1

Tyr Ile Ile Phe Val Tyr Ile Pro Leu
1               5

<210> SEQ ID NO 2
<211> LENGTH: 9
<212> TYPE: PRT
<213> ORGANISM: Human papillomavirus

```
<400> SEQUENCE: 2

Lys Leu Pro Gln Leu Cys Thr Glu Leu
1               5

<210> SEQ ID NO 3
<211> LENGTH: 10
<212> TYPE: PRT
<213> ORGANISM: Human papillomavirus

<400> SEQUENCE: 3

Thr Ile His Asp Ile Ile Leu Glu Cys Val
1               5                   10

<210> SEQ ID NO 4
<211> LENGTH: 9
<212> TYPE: PRT
<213> ORGANISM: Human papillomavirus

<400> SEQUENCE: 4

Tyr Met Leu Asp Leu Gln Pro Glu Thr
1               5

<210> SEQ ID NO 5
<211> LENGTH: 10
<212> TYPE: PRT
<213> ORGANISM: Human papillomavirus

<400> SEQUENCE: 5

Tyr Met Leu Asp Leu Gln Pro Glu Thr Thr
1               5                   10

<210> SEQ ID NO 6
<211> LENGTH: 8
<212> TYPE: PRT
<213> ORGANISM: Human papillomavirus

<400> SEQUENCE: 6

Thr Leu Gly Ile Val Cys Pro Ile
1               5

<210> SEQ ID NO 7
<211> LENGTH: 9
<212> TYPE: PRT
<213> ORGANISM: Human papillomavirus

<400> SEQUENCE: 7

Lys Cys Ile Asp Phe Tyr Ser Arg Ile
1               5

<210> SEQ ID NO 8
<211> LENGTH: 9
<212> TYPE: PRT
<213> ORGANISM: Human papillomavirus

<400> SEQUENCE: 8

Phe Gln Gln Leu Phe Leu Asn Thr Leu
1               5

<210> SEQ ID NO 9
<211> LENGTH: 14
<212> TYPE: PRT
<213> ORGANISM: Homo sapiens

<400> SEQUENCE: 9
```

```
Cys Ala Ala Ser Ser Tyr Asn Gln Gly Gly Lys Leu Ile Phe
1               5                   10

<210> SEQ ID NO 10
<211> LENGTH: 18
<212> TYPE: PRT
<213> ORGANISM: Homo sapiens

<400> SEQUENCE: 10

Cys Ile Leu Arg Asp Val Asn Ala Gly Gly Thr Ser Tyr Gly Lys Leu
1               5                   10                  15

Thr Phe

<210> SEQ ID NO 11
<211> LENGTH: 14
<212> TYPE: PRT
<213> ORGANISM: Homo sapiens

<400> SEQUENCE: 11

Cys Ala Ser Ser Leu Leu Ser Ser Tyr Asn Glu Gln Phe Phe
1               5                   10

<210> SEQ ID NO 12
<211> LENGTH: 12
<212> TYPE: PRT
<213> ORGANISM: Homo sapiens

<400> SEQUENCE: 12

Cys Ala Val Asn Val Asp Phe Asn Lys Phe Tyr Phe
1               5                   10

<210> SEQ ID NO 13
<211> LENGTH: 13
<212> TYPE: PRT
<213> ORGANISM: Homo sapiens

<400> SEQUENCE: 13

Cys Ala Ser Ser Gln Asp Trp Asn Asn Glu Gln Phe Phe
1               5                   10

<210> SEQ ID NO 14
<211> LENGTH: 16
<212> TYPE: PRT
<213> ORGANISM: Homo sapiens

<400> SEQUENCE: 14

Cys Ala Val Gln Ala Asn Arg Gly Ser Thr Leu Gly Arg Leu Tyr Phe
1               5                   10                  15

<210> SEQ ID NO 15
<211> LENGTH: 16
<212> TYPE: PRT
<213> ORGANISM: Homo sapiens

<400> SEQUENCE: 15

Cys Ala Ser Ser Leu Trp Gly Arg Leu Ala Lys Asn Ile Gln Tyr Phe
1               5                   10                  15

<210> SEQ ID NO 16
<211> LENGTH: 13
<212> TYPE: PRT
<213> ORGANISM: Homo sapiens

<400> SEQUENCE: 16
```

```
Cys Ala Val Arg Glu Thr Ser Gly Ser Arg Leu Thr Phe
1               5                   10
```

<210> SEQ ID NO 17
<211> LENGTH: 15
<212> TYPE: PRT
<213> ORGANISM: Homo sapiens

<400> SEQUENCE: 17

```
Cys Ala Ser Ser Phe Trp Gly Arg Ser Thr Asp Thr Gln Tyr Phe
1               5                   10                  15
```

<210> SEQ ID NO 18
<211> LENGTH: 15
<212> TYPE: PRT
<213> ORGANISM: Homo sapiens

<400> SEQUENCE: 18

```
Cys Ala Thr Val Ser Thr Asp Ser Trp Gly Lys Lys Leu Gln Phe
1               5                   10                  15
```

<210> SEQ ID NO 19
<211> LENGTH: 14
<212> TYPE: PRT
<213> ORGANISM: Homo sapiens

<400> SEQUENCE: 19

```
Cys Ala Ile Ser Asp Ser Asn Gly Ile Asn Ile Gln Tyr Phe
1               5                   10
```

<210> SEQ ID NO 20
<211> LENGTH: 16
<212> TYPE: PRT
<213> ORGANISM: Homo sapiens

<400> SEQUENCE: 20

```
Cys Ala Ser Ser Leu Trp Gly Arg Ala Gly Lys Asp Thr Gln Tyr Phe
1               5                   10                  15
```

<210> SEQ ID NO 21
<211> LENGTH: 14
<212> TYPE: PRT
<213> ORGANISM: Homo sapiens

<400> SEQUENCE: 21

```
Cys Ala Val Ser Leu Asn Ser Gly Asn Thr Pro Leu Val Phe
1               5                   10
```

<210> SEQ ID NO 22
<211> LENGTH: 15
<212> TYPE: PRT
<213> ORGANISM: Homo sapiens

<400> SEQUENCE: 22

```
Cys Ser Ala Arg Asp Leu Ala Gly Asn Thr Gly Glu Leu Phe Phe
1               5                   10                  15
```

<210> SEQ ID NO 23
<211> LENGTH: 13
<212> TYPE: PRT
<213> ORGANISM: Homo sapiens

<400> SEQUENCE: 23

```
Cys Gly Thr Gly Thr Asp Ser Trp Gly Lys Leu Gln Phe
1               5                   10
```

```
1               5                   10
```

<210> SEQ ID NO 24
<211> LENGTH: 14
<212> TYPE: PRT
<213> ORGANISM: Homo sapiens

<400> SEQUENCE: 24

```
Cys Ala Ser Ser Pro Gly Leu Ala Gly Gly Glu Gln Phe Phe
1               5                   10
```

<210> SEQ ID NO 25
<211> LENGTH: 14
<212> TYPE: PRT
<213> ORGANISM: Homo sapiens

<400> SEQUENCE: 25

```
Cys Ala Val Glu Pro Asn Ser Gly Asn Thr Pro Leu Val Phe
1               5                   10
```

<210> SEQ ID NO 26
<211> LENGTH: 14
<212> TYPE: PRT
<213> ORGANISM: Homo sapiens

<400> SEQUENCE: 26

```
Cys Ala Ser Ser Leu Ile Ile Ser Tyr Asn Glu Gln Phe Phe
1               5                   10
```

<210> SEQ ID NO 27
<211> LENGTH: 18
<212> TYPE: PRT
<213> ORGANISM: Homo sapiens

<400> SEQUENCE: 27

```
Cys Ala Tyr Arg Ser Ala Pro Tyr Ser Gly Ala Gly Ser Tyr Gln Leu
1               5                   10                  15

Thr Phe
```

<210> SEQ ID NO 28
<211> LENGTH: 16
<212> TYPE: PRT
<213> ORGANISM: Homo sapiens

<400> SEQUENCE: 28

```
Cys Ala Ser Ser Gln Ala Pro Gly Leu Ala Gly Ala Glu Gln Tyr Phe
1               5                   10                  15
```

<210> SEQ ID NO 29
<211> LENGTH: 133
<212> TYPE: PRT
<213> ORGANISM: Homo sapiens

<400> SEQUENCE: 29

```
Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
                20                  25                  30

Gln Glu Gly Asp Ser Ala Val Ile Lys Cys Thr Tyr Ser Asp Ser Ala
            35                  40                  45

Ser Asn Tyr Phe Pro Trp Tyr Lys Gln Glu Leu Gly Lys Gly Pro Gln
        50                  55                  60
```

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Ser
            100                 105                 110

Ser Tyr Asn Gln Gly Gly Lys Leu Ile Phe Gly Gln Gly Thr Glu Leu
            115                 120                 125

Ser Val Lys Pro Asn
    130

<210> SEQ ID NO 30
<211> LENGTH: 133
<212> TYPE: PRT
<213> ORGANISM: Homo sapiens

<400> SEQUENCE: 30

Met Lys Leu Val Thr Ser Ile Thr Val Leu Leu Ser Leu Gly Ile Met
1               5                   10                  15

Gly Asp Ala Lys Thr Thr Gln Pro Asn Ser Met Glu Ser Asn Glu Glu
            20                  25                  30

Glu Pro Val His Leu Pro Cys Asn His Ser Thr Ile Ser Gly Thr Asp
        35                  40                  45

Tyr Ile His Trp Tyr Arg Gln Leu Pro Ser Gln Gly Pro Glu Tyr Val
    50                  55                  60

Ile His Gly Leu Thr Ser Asn Val Asn Asn Arg Met Ala Ser Leu Ala
65                  70                  75                  80

Ile Ala Glu Asp Arg Lys Ser Ser Thr Leu Ile Leu His Arg Ala Thr
                85                  90                  95

Leu Arg Asp Ala Ala Val Tyr Tyr Cys Ile Leu Arg Asp Val Asn Ala
            100                 105                 110

Gly Gly Thr Ser Tyr Gly Lys Leu Thr Phe Gly Gln Gly Thr Ile Leu
            115                 120                 125

Thr Val His Pro Asn
    130

<210> SEQ ID NO 31
<211> LENGTH: 133
<212> TYPE: PRT
<213> ORGANISM: Homo sapiens

<400> SEQUENCE: 31

Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asn Ser Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

```
Ser Ser Leu Leu Ser Ser Tyr Asn Glu Gln Phe Phe Gly Pro Gly Thr
            115                 120                 125

Arg Leu Thr Val Leu
    130

<210> SEQ ID NO 32
<211> LENGTH: 133
<212> TYPE: PRT
<213> ORGANISM: Homo sapiens

<400> SEQUENCE: 32

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asn Ser Gly Pro
            20                  25                  30

Leu Ser Val Pro Glu Gly Ala Ile Ala Ser Leu Asn Cys Thr Tyr Ser
        35                  40                  45

Asp Arg Gly Ser Gln Ser Phe Phe Trp Tyr Arg Gln Tyr Ser Gly Lys
    50                  55                  60

Ser Pro Glu Leu Ile Met Ser Ile Tyr Ser Asn Gly Asp Lys Glu Asp
65                  70                  75                  80

Gly Arg Phe Thr Ala Gln Leu Asn Lys Ala Ser Gln Tyr Val Ser Leu
                85                  90                  95

Leu Ile Arg Asp Ser Gln Pro Ser Asp Ser Ala Thr Tyr Leu Cys Ala
            100                 105                 110

Val Asn Val Asp Phe Asn Lys Phe Tyr Phe Gly Ser Gly Thr Lys Leu
        115                 120                 125

Asn Val Lys Pro Asn
    130

<210> SEQ ID NO 33
<211> LENGTH: 131
<212> TYPE: PRT
<213> ORGANISM: Homo sapiens

<400> SEQUENCE: 33

Met Gly Cys Arg Leu Leu Cys Cys Ala Val Leu Cys Leu Leu Gly Ala
1               5                   10                  15

Val Pro Ile Asp Thr Glu Val Thr Gln Thr Pro Lys His Leu Val Met
            20                  25                  30

Gly Met Thr Asn Lys Lys Ser Leu Lys Cys Glu Gln His Met Gly His
        35                  40                  45

Arg Ala Met Tyr Trp Tyr Lys Gln Lys Ala Lys Lys Pro Pro Glu Leu
    50                  55                  60

Met Phe Val Tyr Ser Tyr Glu Lys Leu Ser Ile Asn Glu Ser Val Pro
65                  70                  75                  80

Ser Arg Phe Ser Pro Glu Cys Pro Asn Ser Ser Leu Leu Asn Leu His
                85                  90                  95

Leu His Ala Leu Gln Pro Glu Asp Ser Ala Leu Tyr Leu Cys Ala Ser
            100                 105                 110

Ser Gln Asp Trp Asn Asn Glu Gln Phe Phe Gly Pro Gly Thr Arg Leu
        115                 120                 125

Thr Val Leu
    130

<210> SEQ ID NO 34
<211> LENGTH: 135
```

```
<212> TYPE: PRT
<213> ORGANISM: Homo sapiens

<400> SEQUENCE: 34

Met Glu Lys Met Leu Glu Cys Ala Phe Ile Val Leu Trp Leu Gln Leu
1               5                   10                  15

Gly Trp Leu Ser Gly Glu Asp Gln Val Thr Gln Ser Pro Glu Ala Leu
            20                  25                  30

Arg Leu Gln Glu Gly Glu Ser Ser Leu Asn Cys Ser Tyr Thr Val
        35                  40                  45

Ser Gly Leu Arg Gly Leu Phe Trp Tyr Arg Gln Asp Pro Gly Lys Gly
    50                  55                  60

Pro Glu Phe Leu Phe Thr Leu Tyr Ser Ala Gly Glu Lys Glu Lys
65              70                  75                  80

Glu Arg Leu Lys Ala Thr Leu Thr Lys Lys Glu Ser Phe Leu His Ile
                85                  90                  95

Thr Ala Pro Lys Pro Glu Asp Ser Ala Thr Tyr Leu Cys Ala Val Gln
            100                 105                 110

Ala Asn Arg Gly Ser Thr Leu Gly Arg Leu Tyr Phe Gly Arg Gly Thr
        115                 120                 125

Gln Leu Thr Val Trp Pro Asp
    130                 135

<210> SEQ ID NO 35
<211> LENGTH: 134
<212> TYPE: PRT
<213> ORGANISM: Homo sapiens

<400> SEQUENCE: 35

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65              70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Ser Leu Trp Gly Arg Leu Ala Lys Asn Ile Gln Tyr Phe Gly Ala Gly
        115                 120                 125

Thr Arg Leu Ser Val Leu
    130

<210> SEQ ID NO 36
<211> LENGTH: 132
<212> TYPE: PRT
<213> ORGANISM: Homo sapiens

<400> SEQUENCE: 36

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
```

```
            20                  25                  30
Pro Glu Gly Glu Asn Leu Val Leu Asn Cys Ser Phe Thr Asp Ser Ala
         35                  40                  45

Ile Tyr Asn Leu Gln Trp Phe Arg Gln Asp Pro Gly Lys Gly Leu Thr
 50                  55                  60

Ser Leu Leu Leu Ile Gln Ser Ser Gln Arg Glu Gln Thr Ser Gly Arg
 65                  70                  75                  80

Leu Asn Ala Ser Leu Asp Lys Ser Ser Gly Arg Ser Thr Leu Tyr Ile
                 85                  90                  95

Ala Ala Ser Gln Pro Gly Asp Ser Ala Thr Tyr Leu Cys Ala Val Arg
            100                 105                 110

Glu Thr Ser Gly Ser Arg Leu Thr Phe Gly Glu Gly Thr Gln Leu Thr
        115                 120                 125

Val Asn Pro Asp
        130

<210> SEQ ID NO 37
<211> LENGTH: 133
<212> TYPE: PRT
<213> ORGANISM: Homo sapiens

<400> SEQUENCE: 37

Met Gly Ile Arg Leu Leu Cys Arg Val Ala Phe Cys Phe Leu Ala Val
 1               5                  10                  15

Gly Leu Val Asp Val Lys Val Thr Gln Ser Ser Arg Tyr Leu Val Lys
             20                  25                  30

Arg Thr Gly Glu Lys Val Phe Leu Glu Cys Val Gln Asp Met Asp His
         35                  40                  45

Glu Asn Met Phe Trp Tyr Arg Gln Asp Pro Gly Leu Gly Leu Arg Leu
 50                  55                  60

Ile Tyr Phe Ser Tyr Asp Val Lys Met Lys Glu Lys Gly Asp Ile Pro
 65                  70                  75                  80

Glu Gly Tyr Ser Val Ser Arg Glu Lys Lys Glu Arg Phe Ser Leu Ile
                 85                  90                  95

Leu Glu Ser Ala Ser Thr Asn Gln Thr Ser Met Tyr Leu Cys Ala Ser
            100                 105                 110

Ser Phe Trp Gly Arg Ser Thr Asp Thr Gln Tyr Phe Gly Pro Gly Thr
        115                 120                 125

Arg Leu Thr Val Leu
        130

<210> SEQ ID NO 38
<211> LENGTH: 133
<212> TYPE: PRT
<213> ORGANISM: Homo sapiens

<400> SEQUENCE: 38

Met Glu Thr Leu Leu Gly Val Ser Leu Val Ile Leu Trp Leu Gln Leu
 1               5                  10                  15

Ala Arg Val Asn Ser Gln Gln Gly Glu Glu Asp Pro Gln Ala Leu Ser
             20                  25                  30

Ile Gln Glu Gly Glu Asn Ala Thr Met Asn Cys Ser Tyr Lys Thr Ser
         35                  40                  45

Ile Asn Asn Leu Gln Trp Tyr Arg Gln Asn Ser Gly Arg Gly Leu Val
 50                  55                  60

His Leu Ile Leu Ile Arg Ser Asn Glu Arg Glu Lys His Ser Gly Arg
```

```
                65                  70                  75                  80
Leu Arg Val Thr Leu Asp Thr Ser Lys Lys Ser Ser Ser Leu Leu Ile
                    85                  90                  95

Thr Ala Ser Arg Ala Ala Asp Thr Ala Ser Tyr Phe Cys Ala Thr Val
                100                 105                 110

Ser Thr Asp Ser Trp Gly Lys Leu Gln Phe Gly Ala Gly Thr Gln Val
                115                 120                 125

Val Val Thr Pro Asp
        130
```

<210> SEQ ID NO 39
<211> LENGTH: 140
<212> TYPE: PRT
<213> ORGANISM: Homo sapiens

<400> SEQUENCE: 39

```
Met Arg Ser Trp Pro Gly Pro Glu Met Gly Thr Arg Leu Phe Phe Tyr
1               5                   10                  15

Val Ala Leu Cys Leu Leu Trp Thr Gly His Met Asp Ala Gly Ile Thr
                20                  25                  30

Gln Ser Pro Arg His Lys Val Thr Glu Thr Gly Thr Pro Val Thr Leu
                35                  40                  45

Arg Cys His Gln Thr Glu Asn His Arg Tyr Met Tyr Trp Tyr Arg Gln
            50                  55                  60

Asp Pro Gly His Gly Leu Arg Leu Ile His Tyr Ser Tyr Gly Val Lys
65                  70                  75                  80

Asp Thr Asp Lys Gly Glu Val Ser Asp Gly Tyr Ser Val Ser Arg Ser
                85                  90                  95

Lys Thr Glu Asp Phe Leu Leu Thr Leu Glu Ser Ala Thr Ser Ser Gln
                100                 105                 110

Thr Ser Val Tyr Phe Cys Ala Ile Ser Asp Ser Asn Gly Ile Asn Ile
                115                 120                 125

Gln Tyr Phe Gly Ala Gly Thr Arg Leu Ser Val Leu
            130                 135                 140
```

<210> SEQ ID NO 40
<211> LENGTH: 134
<212> TYPE: PRT
<213> ORGANISM: Homo sapiens

<400> SEQUENCE: 40

```
Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
                20                  25                  30

Arg Thr Gly Glu Lys Val Phe Leu Glu Cys Val Gln Asp Met Asp His
                35                  40                  45

Glu Asn Met Phe Trp Tyr Arg Gln Asp Pro Gly Leu Gly Leu Arg Leu
            50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
                100                 105                 110

Ser Leu Trp Gly Arg Ala Gly Lys Asp Thr Gln Tyr Phe Gly Pro Gly
```

Thr Arg Leu Thr Val Leu
    130

<210> SEQ ID NO 41
<211> LENGTH: 134
<212> TYPE: PRT
<213> ORGANISM: Homo sapiens

<400> SEQUENCE: 41

Met Leu Leu Leu Val Pro Ala Phe Gln Val Ile Phe Thr Leu Gly
1               5                   10                  15

Gly Thr Arg Ala Gln Ser Val Thr Gln Leu Asp Ser Gln Val Pro Val
            20                  25                  30

Phe Glu Glu Ala Pro Val Glu Leu Arg Cys Asn Tyr Ser Ser Val
        35                  40                  45

Ser Val Tyr Leu Phe Trp Tyr Val Gln Tyr Pro Asn Gln Gly Leu Gln
    50                  55                  60

Leu Leu Leu Lys Tyr Leu Ser Gly Ser Thr Leu Val Glu Ser Ile Asn
65                  70                  75                  80

Gly Phe Glu Ala Glu Phe Asn Lys Ser Gln Thr Ser Phe His Leu Arg
                85                  90                  95

Lys Pro Ser Val His Ile Ser Asp Thr Ala Glu Tyr Phe Cys Ala Val
            100                 105                 110

Ser Leu Asn Ser Gly Asn Thr Pro Leu Val Phe Gly Lys Gly Thr Arg
        115                 120                 125

Leu Ser Val Ile Ala Asn
    130

<210> SEQ ID NO 42
<211> LENGTH: 131
<212> TYPE: PRT
<213> ORGANISM: Homo sapiens

<400> SEQUENCE: 42

Met Leu Leu Leu Leu Leu Leu Gly Pro Gly Ser Gly Leu Gly Ala
1               5                   10                  15

Val Val Ser Gln His Pro Ser Trp Val Ile Cys Lys Ser Gly Thr Ser
            20                  25                  30

Val Lys Ile Glu Cys Arg Ser Leu Asp Phe Gln Ala Thr Thr Met Phe
        35                  40                  45

Trp Tyr Arg Gln Phe Pro Lys Gln Ser Leu Met Leu Met Ala Thr Ser
    50                  55                  60

Asn Glu Gly Ser Lys Ala Thr Tyr Glu Gln Gly Val Glu Lys Asp Lys
65                  70                  75                  80

Phe Leu Ile Asn His Ala Ser Leu Thr Leu Ser Thr Leu Thr Val Thr
                85                  90                  95

Ser Ala His Pro Glu Asp Ser Ser Phe Tyr Ile Cys Ser Ala Arg Asp
            100                 105                 110

Leu Ala Gly Asn Thr Gly Glu Leu Phe Phe Gly Glu Gly Ser Arg Leu
        115                 120                 125

Thr Val Leu
    130

<210> SEQ ID NO 43
<211> LENGTH: 132
<212> TYPE: PRT

<213> ORGANISM: Homo sapiens

<400> SEQUENCE: 43

Met Glu Thr Leu Leu Lys Val Leu Ser Gly Thr Leu Leu Trp Gln Leu
1               5                   10                  15

Thr Trp Val Arg Ser Gln Gln Pro Val Gln Ser Pro Gln Ala Val Ile
            20                  25                  30

Leu Arg Glu Gly Glu Asp Ala Val Ile Asn Cys Ser Ser Ser Lys Ala
        35                  40                  45

Leu Tyr Ser Val His Trp Tyr Arg Gln Lys His Gly Glu Ala Pro Val
    50                  55                  60

Phe Leu Met Ile Leu Leu Lys Gly Gly Glu Gln Lys Gly His Glu Lys
65                  70                  75                  80

Ile Ser Ala Ser Phe Asn Glu Lys Lys Gln Gln Ser Ser Leu Tyr Leu
                85                  90                  95

Thr Ala Ser Gln Leu Ser Tyr Ser Gly Thr Tyr Phe Cys Gly Thr Gly
            100                 105                 110

Thr Asp Ser Trp Gly Lys Leu Gln Phe Gly Ala Gly Thr Gln Val Val
        115                 120                 125

Val Thr Pro Asp
    130

<210> SEQ ID NO 44
<211> LENGTH: 133
<212> TYPE: PRT
<213> ORGANISM: Homo sapiens

<400> SEQUENCE: 44

Met Gly Ser Trp Thr Leu Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asp Tyr Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Pro Gly Leu Ala Gly Gly Glu Gln Phe Phe Gly Pro Gly Thr
        115                 120                 125

Arg Leu Thr Val Leu
    130

<210> SEQ ID NO 45
<211> LENGTH: 131
<212> TYPE: PRT
<213> ORGANISM: Homo sapiens

<400> SEQUENCE: 45

Met Lys Arg Ile Leu Gly Ala Leu Leu Gly Leu Leu Ser Ala Gln Val
1               5                   10                  15

Cys Cys Val Arg Gly Ile Gln Val Glu Gln Ser Pro Pro Asp Leu Ile
            20                  25                  30

```
Leu Gln Glu Gly Ala Asn Ser Thr Leu Arg Cys Asn Phe Ser Asp Ser
            35                  40                  45

Val Asn Asn Leu Gln Trp Phe His Gln Asn Pro Trp Gly Gln Leu Ile
 50                      55                  60

Asn Leu Phe Tyr Ile Pro Ser Gly Thr Lys Gln Asn Gly Arg Leu Ser
 65                  70                  75                  80

Ala Thr Thr Val Ala Thr Glu Arg Tyr Ser Leu Leu Tyr Ile Ser Ser
                     85                  90                  95

Ser Gln Thr Thr Asp Ser Gly Val Tyr Phe Cys Ala Val Glu Pro Asn
                100                 105                 110

Ser Gly Asn Thr Pro Leu Val Phe Gly Lys Gly Thr Arg Leu Ser Val
            115                 120                 125

Ile Ala Asn
    130

<210> SEQ ID NO 46
<211> LENGTH: 133
<212> TYPE: PRT
<213> ORGANISM: Homo sapiens

<400> SEQUENCE: 46

Met Gly Thr Arg Leu Leu Phe Trp Val Ala Phe Cys Leu Leu Gly Ala
  1               5                  10                  15

Tyr His Thr Gly Ala Gly Val Ser Gln Ser Pro Ser Asn Lys Val Thr
                 20                  25                  30

Glu Lys Gly Lys Asp Val Glu Leu Arg Cys Asp Pro Ile Ser Gly His
            35                  40                  45

Thr Ala Leu Tyr Trp Tyr Arg Gln Arg Leu Gly Gln Gly Leu Glu Phe
 50                      55                  60

Leu Ile Tyr Phe Gln Gly Asn Ser Ala Pro Asp Lys Ser Gly Leu Pro
 65                  70                  75                  80

Ser Asp Arg Phe Ser Ala Glu Arg Thr Gly Gly Ser Val Ser Thr Leu
                     85                  90                  95

Thr Ile Gln Arg Thr Gln Gln Glu Asp Ser Ala Val Tyr Leu Cys Ala
                100                 105                 110

Ser Ser Leu Ile Ile Ser Tyr Asn Glu Gln Phe Phe Gly Pro Gly Thr
            115                 120                 125

Arg Leu Thr Val Leu
    130

<210> SEQ ID NO 47
<211> LENGTH: 140
<212> TYPE: PRT
<213> ORGANISM: Homo sapiens

<400> SEQUENCE: 47

Met Ala Cys Pro Gly Phe Leu Trp Ala Leu Val Ile Ser Thr Cys Leu
  1               5                  10                  15

Glu Phe Ser Met Ala Gln Thr Val Thr Gln Ser Gln Pro Glu Met Ser
                 20                  25                  30

Val Gln Glu Ala Glu Thr Val Thr Leu Ser Cys Thr Tyr Asp Thr Ser
            35                  40                  45

Glu Ser Asp Tyr Tyr Leu Phe Trp Tyr Lys Gln Pro Pro Ser Arg Gln
 50                      55                  60

Met Ile Leu Val Ile Arg Gln Glu Ala Tyr Lys Gln Gln Asn Ala Thr
 65                  70                  75                  80
```

```
Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
            100                 105                 110

Ala Tyr Arg Ser Ala Pro Tyr Ser Gly Ala Gly Ser Tyr Gln Leu Thr
            115                 120                 125

Phe Gly Lys Gly Thr Lys Leu Ser Val Ile Pro Asn
        130                 135             140

<210> SEQ ID NO 48
<211> LENGTH: 134
<212> TYPE: PRT
<213> ORGANISM: Homo sapiens

<400> SEQUENCE: 48

Met Gly Cys Arg Leu Leu Cys Cys Ala Val Leu Cys Leu Leu Gly Ala
1               5                   10                  15

Val Pro Met Glu Thr Gly Val Thr Gln Thr Pro Arg His Leu Val Met
                20                  25                  30

Gly Met Thr Asn Lys Lys Ser Leu Lys Cys Glu Gln His Leu Gly His
            35                  40                  45

Asn Ala Met Tyr Trp Tyr Lys Gln Ser Ala Lys Lys Pro Leu Glu Leu
50                  55                  60

Met Phe Val Tyr Asn Phe Lys Glu Gln Thr Glu Asn Asn Ser Val Pro
65                  70                  75                  80

Ser Arg Phe Ser Pro Glu Cys Pro Asn Ser Ser His Leu Phe Leu His
                85                  90                  95

Leu His Thr Leu Gln Pro Glu Asp Ser Ala Leu Tyr Leu Cys Ala Ser
            100                 105                 110

Ser Gln Ala Pro Gly Leu Ala Gly Ala Glu Gln Tyr Phe Gly Pro Gly
            115                 120                 125

Thr Arg Leu Thr Val Thr
130
```